(12) United States Patent
Robertson et al.

(10) Patent No.: US 11,959,858 B2
(45) Date of Patent: Apr. 16, 2024

(54) METHOD AND SYSTEM FOR HIGH-THROUGHPUT SCREENING

(71) Applicant: Virginia Tech Intellectual Properties, Inc., Blacksburg, VA (US)

(72) Inventors: John L. Robertson, Floyd, VA (US); Ryan Senger, North Chesterfield, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 246 days.

(21) Appl. No.: 17/345,735

(22) Filed: Jun. 11, 2021

(65) Prior Publication Data

US 2021/0389251 A1 Dec. 16, 2021

Related U.S. Application Data

(60) Provisional application No. 63/037,714, filed on Jun. 11, 2020.

(51) Int. Cl.
*G01N 33/493* (2006.01)
*G01N 21/65* (2006.01)
(Continued)

(52) U.S. Cl.
CPC ..... *G01N 21/658* (2013.01); *G01N 33/48771* (2013.01); *G01N 33/493* (2013.01);
(Continued)

(58) Field of Classification Search
CPC ....... G16H 10/40; G01N 33/493; G01N 21/65
See application file for complete search history.

(56) References Cited

U.S. PATENT DOCUMENTS

| 3,598,727 A | 8/1971 | Willock |
| 4,172,033 A | 10/1979 | Willock |

(Continued)

FOREIGN PATENT DOCUMENTS

| EP | 1637586 A2 * | 3/2006 | ............ C12M 41/34 |
| WO | WO-2007011571 A2 * | 1/2007 | ............ G01N 21/65 |

(Continued)

OTHER PUBLICATIONS

Stemcell Technologies, "Loading the RoboSep™-S Carousel and Starting a Run" https://www.youtube.com/watch?v=uhMR_xheVik hereafter Stem Cell Technologies (Year: 2017).*

(Continued)

*Primary Examiner* — Maurice C Smith

(74) *Attorney, Agent, or Firm* — New River Valley IP Law, P.C.; Michele L. Mayberry; Ashley M. Gates

(57) ABSTRACT

Chronic Kidney Disease (CKD) is characterized by the progressive loss of renal function which eventually leads to End Stage Renal Disease (ESRD). CKD affects roughly 30 million Americans, costs billions of dollars in healthcare spending annually, and leaves thousands of patients reliant on burdensome dialysis treatments while waiting for a transplant. Fortunately, CKD may be controllable if diagnosed early in the disease progression. RAMETRIX™ is a novel public health screening technology for early diagnosis and detection of CKD. This technology uses Raman spectroscopy and chemometrics to analyze the molecular composition of urine and other biological fluids. RAMETRIX™ is a fast, non-invasive, accurate, and inexpensive diagnostic tool that can revolutionize the way healthcare providers detect and treat CKD. The RAMETRIX™ AutoScanner is a system enabling more efficient sample processing in large-scale settings such as hospitals and medical laboratories.

18 Claims, 20 Drawing Sheets

(51) Int. Cl.
　　　*G01N 33/487*　　(2006.01)
　　　*G01N 33/50*　　(2006.01)
　　　*G16H 10/40*　　(2018.01)

(52) U.S. Cl.
　　　CPC ......... *G01N 33/5091* (2013.01); *G16H 10/40* (2018.01); *G01N 2800/00* (2013.01)

(56) References Cited

U.S. PATENT DOCUMENTS

| | | |
|---|---|---|
| 4,267,040 A | 5/1981 | Schal |
| 4,769,134 A | 9/1988 | Allan et al. |
| 5,112,127 A | 5/1992 | Carrabba et al. |
| 5,507,723 A | 4/1996 | Keshaviah |
| 5,534,997 A | 7/1996 | Schrader |
| 5,553,616 A | 9/1996 | Ham et al. |
| 5,786,893 A | 7/1998 | Fink et al. |
| 6,100,975 A | 8/2000 | Smith et al. |
| 6,151,522 A | 11/2000 | Alfano et al. |
| 6,284,131 B1 | 9/2001 | Hogard et al. |
| 6,632,680 B1 * | 10/2003 | DesLauriers ........ G01N 21/359 436/171 |
| 7,326,576 B2 | 2/2008 | Womble et al. |
| 7,505,128 B2 | 3/2009 | Zribi et al. |
| 7,524,671 B2 | 4/2009 | Clarke et al. |
| 7,651,851 B2 | 1/2010 | Clarke et al. |
| 8,125,623 B2 | 2/2012 | Munger et al. |
| 8,133,194 B2 | 3/2012 | Szamosfalvi et al. |
| 8,638,431 B2 | 1/2014 | Ashok et al. |
| 8,699,020 B1 | 4/2014 | Zhou et al. |
| 8,945,936 B2 | 2/2015 | Ash et al. |
| 8,953,159 B2 | 2/2015 | Cunningham et al. |
| 9,089,126 B2 | 7/2015 | Faulkner et al. |
| 9,215,985 B2 | 12/2015 | Gross et al. |
| 9,267,845 B2 | 2/2016 | Ichijyo et al. |
| 9,550,020 B2 | 1/2017 | Kelly et al. |
| 9,713,666 B2 | 7/2017 | Pudil et al. |
| 11,324,869 B2 | 5/2022 | Robertson et al. |
| 11,674,903 B2 | 6/2023 | Robertson et al. |
| 2006/0281068 A1 | 12/2006 | Maier et al. |
| 2007/0109535 A1 | 5/2007 | Maier et al. |
| 2008/0097272 A1 | 4/2008 | Daniel et al. |
| 2008/0158544 A1 | 7/2008 | Womble et al. |
| 2010/0070197 A1 | 3/2010 | Wang et al. |
| 2010/0165324 A1 | 7/2010 | Womble et al. |
| 2012/0008130 A9 | 1/2012 | Munger et al. |
| 2012/0099102 A1 | 4/2012 | Bello |
| 2012/0276549 A1 | 11/2012 | Cunningham et al. |
| 2013/0056418 A1 | 3/2013 | Kopperschmidt et al. |
| 2014/0052386 A1 | 2/2014 | Guenther et al. |
| 2014/0098359 A1 | 4/2014 | Gross et al. |
| 2016/0252459 A1 * | 9/2016 | Bell .................... G01N 21/658 506/9 |
| 2017/0045455 A1 | 2/2017 | Robertson et al. |
| 2021/0215610 A1 | 7/2021 | Robertson et al. |
| 2021/0270742 A1 | 9/2021 | Senger et al. |
| 2021/0389251 A1 | 12/2021 | Robertson et al. |
| 2022/0040390 A1 | 2/2022 | Robertson et al. |
| 2023/0147592 A1 | 5/2023 | Robertson et al. |

FOREIGN PATENT DOCUMENTS

| | | | |
|---|---|---|---|
| WO | 2012140022 A1 | 10/2012 | |
| WO | 2015164620 A1 | 10/2015 | |
| WO | WO-2016004322 A2 * | 1/2016 | ............ C12M 41/32 |
| WO | 2020176663 A1 | 9/2020 | |

OTHER PUBLICATIONS

AcuTech Scientific Inc, "The World Highest Reproducible Raman Spectrometer: AcuScan 1500 Manual(2:22)", 2014 hereafter AcuTech (Year: 2014).*

Thermo Fisher Scientific, "DXR SmartRaman Spectrometer", 2017 (Year: 2017).*

J. Renwick, "Prediction of Adipose Tissue Composition Using Raman Spectroscopy: Average Properties and Individual Fatty Acids", 2006 (Year: 2006).*

(Robertson, John et al.) Co-pending U.S. Appl. No. 17/146,301, filed Jan. 11, 2021, Specification, claims, figures.

(Robertson, John L. et al) Co-pending International Application No. PCT/US20/19964, filed Feb. 26, 2020, Specification, Claims, Figures.

(Robertson, John L. et al.) Co-pending U.S. Appl. No. 15/305,940, filed Oct. 21, 2016, Specification, Claims, and Figures.

(Robertson, John L. et al.) Co-pending U.S. Appl. No. 17/434,294, filed Aug. 26, 2021, Specification, Claims, and Figures.

(Robertson, John L. et al.) Co-Pending International Application No. PCT/US2015/027323, filed Apr. 23, 2015 and published as WO2015164620 on Oct. 29, 2015, Specification, Claims, Figures.

(Senger, R et al.) Co-Pending U.S. Appl. No. 17/188,737, filed Mar. 1, 2021, Specification, Drawings, and Claims.

Athamneh, A.I.M. and Senger R.S. Peptide-Guided Surface-Enhanced Raman Scattering Probes for Localized Cell Composition Analysis. Appl Env Microbiol. 2012;78: 7805-7808.

Athamneh, A.I.M et al., Phenotypic Profiling of Antibiotic Response Signatures in *Escherichia coli* Using Raman Spectroscopy. Antimicrob Agents Chemother. 2014;58: 1302-1314.

Bird, B. et al., Cytology by Infrared Micro-Spectroscopy: Automatic Distinction of Cell Types in Urinary Cytology. Vib Spectrosc. 2008;48: 101-106, 15 pages.

Bouatra, S. et al. The Human Urine Metabolome. PLOS ONE. 2013;8: e73076, 25 pages.

Cai, T.T. et al. "Enhanced Chemical Classification of Raman Images Using Multiresolution Wavelet Transformation". Appl. Spectrosc. 2001. 55(9): 1124-1130.

Cai, Y. et al. "Baseline correction for Raman spectra using penalized spline smoothing based on vector transformation". Anal. Methods. 2018. 10(28): 3525-3533.

Candeloro, P. et al. "Raman database of amino acids solutions: A critical study of extended multiplicative signal correction". Analyst. 2013. 138(24): 7331-7340).

Canetta, E. et al., Modulated Raman spectroscopy for enhanced identification of bladder tumor cells in urine samples. J Biomed Opt. 2011; 16(3): 037002, 8 pages.

Centers for Disease Control and Prevention, National Chronic Kidney Disease Factsheet, 2014, 4 pages.

Chen, D. et al. "Adaptive wavelet transform suppresses background and noise for quantitative analysis by Raman spectrometry". Anal. Bioanal. Chem. 2011. 400(2): 625-634.

Chiu, Y.C. et al., Enhanced Raman sensitivity and magnetic separation for urolithiasis detection using phosphonic acid-terminated Fe3O4 nanoclusters. J. Mater. Chem. B 2015(3):4282-4290.

Collins, AJ et al., "Death, hospitalization, and economic associations among incident hemodialysis patients with hematocrit values of 36 to 39%," J Am Soc Nephrol 12(11):2465-73, 2001.

Co-pending U.S. Appl. No. 15/305,940, Final Office Action dated Jul. 13, 2020, 22 pages.

Co-pending U.S. Appl. No. 15/305,940, Non-Final Office Action dated May 7, 2021, 24 pages.

Co-pending U.S. Appl. No. 15/305,940, Non-Final Office Action dated Nov. 1, 2019, 16 pages.

Co-pending U.S. Appl. No. 15/305,940, Response to Jul. 13, 2020 Final Office Action, filed Oct. 13, 2020, 11 pages.

Co-pending U.S. Appl. No. 15/305,940, Response to Mar. 27, 2019 Restriction Requirement, filed Sep. 27, 2019, 9 pages.

Co-pending U.S. Appl. No. 15/305,940, Response to May 7, 2021 Non-Final Office Action, filed Sep. 7, 2021, 14 pages.

Co-pending U.S. Appl. No. 15/305,940, Response to Nov. 1, 2019 Non-Final Office Action, filed May 1, 2020, 13 pages.

Co-pending U.S. Appl. No. 15/305,940, Restriction Requirement dated Mar. 27, 2019, 9 pages.

Daugirdas, John T. et al. "Improved equation for estimating single-pool Kt/V at higher dialysis frequencies", Nephrol Dial Transplant (2013) 28: 2156-2160.

(56) References Cited

OTHER PUBLICATIONS

Daugirdas, John T. et al. "Surface-Area-Normalized Kt/V: A Method of Rescaling Dialysis Dose to Body Surface Area-Implications for Different-Size Patients by Gender", Semin Dial. 2008; 21(5): 415-421, 17 pages.

Depciuch, J. et al. "Application of Raman Spectroscopy and Infrared Spectroscopy in the Identification of Breast Cancer". Appl. Spectrosc. 2016. 70(2): 251-263.

Dobre, M, Meyer, TW, Hostetter, TH, "Searching for uremic toxins," Clin J Am Soc Nephrol 8: 322-327, 2013.

Duranton, F et al., "Normal and pathological concentrations of uremic toxins," J Am Soc Nephrol 23: 1258-1270, 2012.

Eknoyan, G. et al., "Effects of dialysis dose and membrane flux in maintenance hemodialysis," New Engl Journ Med 347: 2010-2019, 2002.

Gautam, R. et al. "Review of multidimensional data processing approaches for Raman and infrared spectroscopy". EPJ Techn. Instrum. 2015. 2(1): 8, 38 pages.

He, S. et al. "Baseline correction for Raman spectra using an improved asymmetric least squares method". Anal. Methods. The Royal Society of Chemistry, 2014. 6(12): 4402-4407.

Huttanus, H. et al. "Raman Chemometric Urinalysis (Rametrix™) as a screen for bladder cancer," PLoS One. 2020; 15(8): e0237070. Published online Aug. 21, 2020.

Hyde, F.W. et al., "Detection of antigens in urine of mice and humans infected with Borrelia burgdorferi, etiologic agent of Lyme disease," J Clin Microbiol 27, 58-61 (1989).

Ito, S, Yoshida, M, "Review: Protein-bound uremic toxins: new culprits of cardiovascular events in chronic kidney disease patients," Toxins 6: 665-678, 2014; doi:I0.3390/toxins6020665.

Jaejin Kim et al., "Feasibility Study for the Monitoring of Ureain Dialysate Solution using Raman Spectroscopy", Bull. Korean Chem. Soc. 2011, vol. 32, No. 3 805-808.

Jha, V. et al., "Chronic kidney disease: global dimension and perspectives", The Lancet, 2013, 382(9888), 260-272.

Lee, S. et al., "Improving Clearance for Renal Replacement Therapy", Kidney 360 Publish Ahead of Print, published May 12, 2021, 32 pages.

Levey, AS et al., "Controlling the epidemic of cardiovascular disease in chronic renal disease: What do we need to learn? Where do we go from here?," Amer J Kid Disease 32: 853-906, 1998.

Li, J. et al. "Wavelet transform based on the optimal wavelet pairs for tunable diode laser absorption spectroscopy signal processing". Appl. Spectrosc. 2015. 69(4): 496-506.

Liabeuf, S, Drukke, TB, Massay, ZA, "Protein-bound uremic toxins: new insight from clinical studies," Toxins 3: 911-919, 2011.

Liland, K. et al. "Model-based pre-processing in Raman spectroscopy of biological samples". J. Raman Spectrosc. 2016. 47(6): 643-650.

Liland, K. et al. "Optimal Choice of Baseline Correction for Multivariate Calibration of Spectra" Appl. Spectrosc. 2010, 64: 1007-1016.

Liu, J. et al. "Goldindec: A Novel Algorithm for Raman Spectrum Baseline Correction". Appl. Spectrosc. 2015. 69(7): 834-842.

Magni, R. et al., "Application of Nanotrap technology for high sensitivity measurement of urinary outer surface protein A carboxyl terminus domain in early stage Lyme borreliosis," J Transl Med (2015) 13: 346, 22 pages.

Mahadevan-Jansen, A. and Richards-Kortum, R.R. "Raman spectroscopy for the detection of cancers and precancers". J. Biomed. Opt. 1996. 1(1): 31-70.

Mazet, V. et al. "Background removal from spectra by designing and minimising a non-quadratic cost function". Chemom. Intell. Lab. Syst. 2005. 76(2): 121-133.

Meyer, T. W. et al., "Dialysis Cannot be Dosed", Semin Dial. 2011; 24(5): 471-479, 19 pages.

Balan et al. "Vibrational spectroscopy fingerprinting in medicine: from molecular to clinical practice." Materials 12.18 (2019): 2884, 40 pages.

Co-pending U.S. Appl. No. 15/305,940, Final Office Action dated Dec. 1, 2021, 27 pages.

Meyer, TW, Hostetter, TH, "Uremia", New Engl J Med 357: 1316-1325, 2007.

Minka "A statistical learning/pattern recognition glossary." Retrieved Jun. 29 (2005): 2008. Available online http://alumni.media.mit.edu/~tpminka/statlearn/glossary/glossary.htm., accessed Jul. 1, 2020 (Year: 2005).

Mosier-Boss, P.A. et al. "Fluorescence rejection in Raman spectroscopy by shifted-spectra, edge detection, and FFT filtering techniques". Appl. Spectrosc. 1995. 49: 630-638.

Movasaghi, Z. et al., Raman Spectroscopy of Biological Tissues. Appl Spectrosc Rev. 2007;42: 493-541.

PCT Application No. PCT/US2015/027323 International Search Report and Written Opinion dated Sep. 8, 2015, 11 pages.

Pegalajar-Jurado, A. et al., (2018) "Identification of urine metabolites as biomarkers of early Lyme Disease," Nature Scientific Reports 8:12204, 12 pages.

Pending International Application No. PCT/US20/19964, International Search Report and Written Opinion dated May 22, 2020, 7 pages.

Peng, J. et al. "Asymmetric least squares for multiple spectra baseline correction". Anal. Chim. Acta. 2010. 683(1): 63-68.

Rauter, C. et al., "Critical evaluation of urine-based PCR assay for diagnosis of Lyme borreliosis," Clin Diagn Lab Immunol 12: 910-917 (2005).

Scholtes-Timmerman, M. et al. "A novel approach to correct variations in Raman spectra due to photo-bleachable cellular components". Analyst. 2009. 134(2): 387-393.

Schulze, G. et al. "Investigation of selected baseline removal techniques as candidates for automated implementation". Appl. Spectrosc. 2005. 59(5): 545-574.

Senger, R.S. and Robertson, J.L. "The RametrixTM PRO Toolbox v1.0 for MATLAB®". PeerJ. 2020. 8: e8179.

Senger, R.S. et al. "Spectral characteristics of urine from patients with end-stage kidney disease analyzed using Raman Chemometric Urinalysis (Rametrix)". PLoS One. 2020. 15(1): e0227281).

Senger, R.S. et al. "Spectral characteristics of urine specimens from healthy human volunteers analyzed using Raman chemometric urinalysis (Rametrix)". PLoS One. 2019. 14(9): e0222115.

Senger, R.S., Kavuru, V., Sullivan, M., Gouldin, A., Lundgren, S., Merrifield, K. (2019), Spectral characteristics of urine specimens from healthy human volunteers analyzed using Raman chemometric urinalysis (Rametrix). PLoS ONE 14(9): e0222115.

Senger, R.S., Sullivan, M., Gouldin, A., Lundgren, S., Merrifield, K., Steen, C., Spectral characteristics of urine from patients with end-stage kidney disease analyzed using Raman Chemometric Urinalysis (Rametrix) PLoS ONE 15(1): e0227281, 2020.

Shapiro, A. et al., Raman molecular imaging: a novel spectroscopic technique for diagnosis of bladder cancer in urine specimens. Eur Urol. 2011;59: 106-112.

Shinzawa, H. et al., "Multivariate data analysis for Raman spectroscopic imaging" Journal of Raman Spectroscopy, 2009, 40:1720-1725.

Vanholder, R, et al., European Uremic Toxin Work Group (EUTox), "Review on uremic toxins: classification, concentration, and interindividual variability," Kidney Int. May 2003;63(5):1934-43, 2003.

Ward, R. A. et al., "Dialysate Flow Rate and Delivered Kt/Vurea for Dialyzers with Enhanced Dialysate Flow Distribution", Clin J Am Soc Nephrol 6: 2235-2239, Sep. 2011.

Yang, Y.T. et al., Off-Resonance SERS Nanoprobe-Targeted Screen of Biomarkers for Antigens Recognition of Bladder Normal and Aggressive Cancer Cells. Analytical Chemistry 2019;91(13): 8213-8220.

Zu, T.N.K. et al., Near-Real-Time Analysis of the Phenotypic Responses of *Escherichia coli* to 1-Butanol Exposure Using Raman Spectroscopy. J Bacteriol. 2014;196: 3983-3991.

Su, H. et al., "Renal histopathological analysis of 26 postmortem findings of patients with COVID-19 in China", Kidney Int. 2020; 98: 219-227.

(56) References Cited

OTHER PUBLICATIONS

Turi, K. N. et al., "A review of metabolomics approaches and their application in identifying casual pathways of childhood asthma", J. Allergy Clin. Immunol. 2018; 141(4):1191-1201, 48 pages.

Wang, N. et al. "Recent advances in spontaneous Raman spectroscopic imaging: Instrumentation and applications" Current Medicinal Chemistry, vol. 27, No. 36, 2020, pp. 6188-6207(20), Available online Jul. 26, 2019, Abstract only.

Xu and Du, (Jul. 27-Aug. 1, 2019). ISREA:A Novel Approach for Raman Spectrum Baseline Correction and Its Application on Real Data [abstract]. JSM 2019, Denver, CO. [Retrieved online Nov. 14, 2023] (Year: 2019).

Xu, Y. et al., "Sparse logistic regression on functional data", Stat. Interface, vol. 0 (2021) 1, 9 pages.

Zhang, D. and Ben-Amotz, D. "Enhanced Chemical Classification of Raman Images in the Presence of Strong Fluorescence Interference". Appl. Spectrosc. OSA, 2000, 54(9): 1379-1383, Abstract only.

Zhao, J. et al. "Automated autofluorescence background subtraction algorithm for biomedical Raman spectroscopy". Appl. Spectrosc. 2007. 61(11): 1225-1232, Abstract only.

Zu, T.N.K. et al., Assessment of ex vivo Perfused Liver Health by Raman Spectroscopy. J Raman Spectrosc. 2015; 46: 551-558, Abstract only.

(Robertson, John L. et al.) Co-Pending U.S. Appl. No. 17/982,019, filed Nov. 7, 2022, Specification, Drawings, and Claims.

Afseth, N.K. and Kohler, A. "Extended multiplicative signal correction in vibrational spectroscopy, a tutorial". Chemometrics and Intelligent Laboratory Systems. 2012. 117: 92-99. 10.1016/j.chemolab. 2012.03.004, Abstract only.

Batlle, D. et al. "Acute Kidney Injury in COVID-19: Emerging Evidence of a Distinct Pathophysiology", J. Am. Soc. Nephrol. 2020; 31: 1380-1383.

Beattie, J.R. and McGarvey, J.J. "Estimation of signal backgrounds on multivariate loadings improves model generation in face of complex variation in backgrounds and constituents". J of Raman Spectrosc. 2013. 44(2): 329-338. 10.1002/jrs.4178, Abstract only.

Bispo, J. et al. "Correlating the amount of urea, creatinine, and glucose in urine from patients with diabetes mellitus and hypertension with the risk of developing renal lesions by means of Raman spectroscopy and principal component analysis", Journal of Biomedical Optics 18(8), 087004 (Aug. 2013), 8 pages.

Castelli, F. A. et al., "Metabolomics for personalized medicine: the input of analytical chemistry from biomarker discovery to point-of-care tests", Anal. Bioanal. Chem. 414, 759-789 (2022).

Chen, Y. T. et al., "Mortality rate of acute kidney injury in SARS, MERS, and COVID-19 infection: A systematic review and meta-analysis", Crit. Care 2020; 24: 439, 4 pages.

Chen, Z. and Kim, J. "Urinary proteomics and metabolomics studies to monitor bladder health and urological diseases", BMC Urol. 2016; 16 (Mar 22): 11, 13 pages.

Cheng, S. et al., "Potential impact and study considerations of metabolomics in cardiovascular health and disease: A scientific statement from the American Heart Association", Circ. Cardiobasc. Genet. 2017; 10(2): e000032, 13 pages.

Cheng, Y. et al., "Kidney disease is associated with in-hospital death of patients with COVID-19", Kidney Int. 2020; 97: 829-838.

Co-pending U.S. Appl. No. 15/305,940, Applicant-Initiated Interview Summary dated Mar. 28, 2022, 3 pages.

Co-pending U.S. Appl. No. 15/305,940, Applicant-Initiated Interview Summary, dated Jan. 18, 2023, 4 pages.

Co-pending U.S. Appl. No. 15/305,940, Final Office Action dated Dec. 22, 2022, 18 pages.

Co-pending U.S. Appl. No. 15/305,940, Non-Final Office Action dated Jun. 2, 2022, 37 pages.

Co-pending U.S. Appl. No. 15/305,940, Notice of Allowance dated Feb. 1, 2023, 7 pages.

Co-pending U.S. Appl. No. 15/305,940, Response After Final Office Action, dated Jan. 13, 2023, 6 pages.

Co-pending U.S. Appl. No. 15/305,940, Response to Dec. 1, 2021 Final Office Action, dated Feb. 25, 2022, 17 pages.

Co-pending U.S. Appl. No. 15/305,940, Response to Jun. 2, 2022 Non-Final Office Action, dated Dec. 2, 2022, 31 pages.

Co-pending U.S. Appl. No. 15/305,940, Rule 132 Affidavit dated Dec. 2, 2022, 23 pages.

Co-Pending U.S. Appl. No. 17/146,301, Non-final Office Action dated Jun. 13, 2023, 27 pages.

Co-Pending U.S. Appl. No. 17/146,301, Response to Notice to File Corrected Application Papers filed Feb. 8, 2021, 228 pages.

Co-pending U.S. Appl. No. 17/434,294, Notice of Allowance dated Dec. 29, 2021, 11 pages.

Das, R.S. and Agrawal, Y.K. "Raman spectroscopy: Recent advancements, techniques and applications". Vib. Spectrosc. 2011. 57(2): 163-176, Abstract only.

Dator, R. et al., "Metabolomics profiles of smokers from two ethnic groups with differing lung cancer risk", Chem. Res. Toxicol. 2020; 33(8):2087-2098.

Del Mistro, G. et al. "Surface-enhanced Raman spectroscopy of urine for prostate cancer detection: a preliminary study", Analytical Bioanalytical Chemistry, 407, 3271-3275, 2015.

Eilers, P.H.C. "A perfect smoother". Anal. Chem. 2003. 75(14): 3631-3636, Abstract only.

Emwas, A. H. et al., "Standardizing the experimental conditions for using urine in NMR-based metabolomic studies with a particular focus on diagnostic studies: a review", Metabolomics 2015; 11(4): 872-894.

Fisher, A. K. et al. "Raman Chemometrics and Application to Enzyme Kinetics and Urinalysis" [Doctoral dissertation, Virginia Tech], 142 pages, , 2018.

Fisher, A.K. et al. "The RametrixTM Lite Toolbox v1.0 for Mathlab®". J. Raman Spectrosc. 2018, 49(5): 885-896, Abstract only.

Fisher, M. et al., "AKI in hospitalized patients with and without COVID-19: A comparison study", J. Am. Soc. Nephrol. 2020; 31: 2145-2157.

Gowda, G. A. et al., "Metabolomics-based methods for early disease diagnostics", Expert Rev. Mol. Diagn. 2008; 8 (5):617-633, 28 pages.

Hassler, L. et al., "Evidence for and against direct kidney infection by SARS-CoV-2 in patients with COVID-19", CJASN 2021; 16, 1755-1765, 2021.

Hirsch, J. S. et al., "Acute kidney injury in patients hospitalized with COVID-19", Kidney Int. 2020; 98: 209-218.

Kerr, L.T. et al., Methodologies for bladder cancer detection with Raman based urine cytology. Analytical Methods, 2016;8: 4991-5000, Abstract only.

Lafuente, B. et al., "The power of databases: the RRUFF project". In: T. Armbruster, R.M. Danisi, editors. Highlights in Mineralogical Crystallography. W. De Gruyter, Berlin, Germany, 2015, 32 pages.

Lieber, C.A. and Mahadevan-Jansen, A. "Automated Method for Subtraction of Fluorescence from Biological Raman Spectra". Appl. Spectrosc. 2003. 57: 1363-1367, Abstract only.

Lo, P.A. et al., Automatic Raman spectroscopic urine crystal identification system using fluorescent image-guided 2D scanning platform with Fe3O4 crystal violet nanoclusters. J Raman Spectrosc 2018;50(1)34-50, Abstract only.

Martens, H. and Stark, E. "Extended multiplicative signal correction and spectral interference subtraction: new preprocessing methods for near infrared spectroscopy." J. Pharm. Biomed. Anal. 1991. 9 8: 625-635, Abstract only.

Mohamed, M. M. et al., "Acute kidney injury associated with coronavirus disease 2019 in urban New Orleans", Kidney360 2020; 1: 614-622, 19 pages.

Moledina, D. G. et al., "The association of COVID-19 with acute kidney injury independent of severity of illness: A multicenter cohort study", Am. J. Kidney Dis. 2021; 77: 490-499.e1, 12 pages.

Murugan, R. and Kellum, J. A., "Acute kidney injury: what's the prognosis?" Nat. Rev. Nephrol. 2011; 7(4): 209-217.

Ng, J. H. et al., "Pathophysiology and pathology of acute kidney injury in patients with COVID-19", Adv. Chronic Kidney Dis. 2020; 27: 365-376.

(56) References Cited

OTHER PUBLICATIONS

Pei, G. et al., "Renal involvement and early prognosis in patients with COVID-19 pneumonia", J. Am. Soc. Nephrol. 2020; 31: 1157-1165.
Richardson, S. et al., "Presenting characteristics, comorbidities, and outcomes among 5700 patients hospitalized with COVID-19 in the New York City area", JAMA 2020; 323: 2052-2059.
Robertson, J. L. et al. (2022), "Alterations in the molecular composition of COVID-19 patient urine, detected using Raman spectroscopic/computational analysis", PLOS ONE 17(7): e0270914, 16 pages.
Senger, R.S. and Scherr, D., "Resolving complex phenotypes with Raman spectroscopy and chemometrics", Curr. Opin. Biotechnol. 2020; 66:277-282, 16 pages.
Sharma, P. et al., "COVID-19-associated kidney injury: A case series of kidney biopsy findings", J. Am. Soc. Nephrol. 2020; 31: 1948-1958.
Shen, Y. et al., "Raman imaging of small biomolecules", Annu. Rev. Biophys. 2019; 48:347-369.
Shusterman, V. et al. "Enhancing the precision of ECG baseline correction: selective filtering and removal of residual error". Comput. Biomed. Res. 2000. 33(2): 144-160, Abstract only.
Stellman, C.M. et al. Multivariate Raman Imaging of Simulated and "Real World Glass-Reinforced Composites". Appl. Spectrosc. 1996. 50: 552-557, Abstract only.

* cited by examiner

METHOD AND SYSTEM FOR HIGH-THROUGHPUT SCREENING

CROSS-REFERENCE TO RELATED APPLICATIONS

This application relies on the disclosure of and claims priority to and the benefit of the filing date of U.S. Provisional Application No. 63/037,714 filed Jun. 11, 2020, which is hereby incorporated by reference herein in its entirety.

BACKGROUND OF THE INVENTION

Field of the Invention

The present invention relates to the field of disease detection and characterization. More particularly, the present invention relates to methods of high-throughput screening of one or more types of liquid samples, such as screening of urine samples for chronic kidney disease or other diseases such as diabetes mellitus that alter urine composition. These are only examples and not an inclusive list of potential disease targets.

Description of Related Art

The iRICELL Series Urinalysis Workcell is a two-component automated urinalysis system, composed of the iChemVELOCITY Urine Chemistry System and the iQ200 Series Urine Microscopic System. Connected together, the iRICELL is able to analyze a wide range of chemicals and biological parameters. More specifically, the iChemVELOCITY part of the system is mainly responsible for the analysis of chemicals, such as ketones, glucose, and proteins, but it is also able to detect other parameters including pH, specific gravity, and blood concentration. The iQ200, on the other hand, is responsible for the microbiological analysis, including the detection of red and white blood cells, and microorganisms such as bacteria. Most importantly, this system is based on the use of dry chemistry, or urine testing through a testing strip, and it is marked by its high throughput and high accuracy when testing a wide range of parameters. It is, however, relatively expensive.

The Thermo Fisher Scientific DXR™3 SmartRaman Spectrometer is a multipurpose analytical device using Raman spectroscopy. Thermo Fisher emphasizes the device's ability to perform bulk-sample analysis (analysis of macro-samples), and it is completely automated and very versatile. According to Thermo Fisher, it can analyze fluids through different containers, such as glass vials, bottles, jars, plastic bags, and well plates. Coupled with the Thermo Scientific™OMNIC™ Spectra Software and other software systems, it detects microparticles efficiently in a wide variety of areas, including pharmacology, forensics, and nanotechnology. This system, though, is not specialized in urinalysis, so it is not as reliable as the iRICELL system or the AutoScanner, both of which specialize in urinalysis.

The present invention comprises numerous unprecedented features. First, the system comprises an innovative combination of automated urinalysis and Raman scanning techniques. Second, the AutoScanner specializes in urinalysis, but it is not restricted to urinalysis. In embodiments, a patient sample is preferably dialysate, blood, plasma, or urine, but can be any sample from or associated with a patient. The system can also be used in the examination of other fluids, such as water and alcohol, for numerous applications including quality monitoring. In addition, this device can significantly lower the cost for high throughput urinalysis.

SUMMARY OF THE INVENTION

The present invention provides a system for high-throughput Raman spectra collection to allow for efficient sample processing. Features of the system guide a user to ensure proper sample labeling and prevent data mismatches. The system uses Raman spectroscopy and chemometrics to analyze the molecular composition of urine and other fluids. RAMETRIX™ is a fast, non-invasive, accurate, and inexpensive diagnostic tool to detect disease.

Included in embodiments of the invention is Aspect 1, which encompasses a system comprising a Raman spectrometer; one or more sample carousel; a computer with a processor and memory; and one or more set of computer-executable instructions capable of: controlling the Raman spectrometer to obtain Raman spectral data on samples; controlling one or more of the sample carousels; and performing one or more chemometric analyses on the Raman spectral data.

Aspect 2 is the system of Aspect 1, wherein one or more of the chemometric analyses comprises identifying whether a urine sample is classified as being (a) from a subject who has a specified condition or (b) from a subject who does not have the specified condition, and is performed by determining that the Raman spectral data of the urine sample fits closer mathematically to one or the other statistically significant groups (a) or (b).

Aspect 3 is the system of Aspects 1 or 2, wherein the specified condition is any one or more of Bladder cancer (all types, grades, and stages); Acute cystitis (all types, grades, stages, and etiologies, including infectious and non-infectious etiologies); Chronic cystitis (all types, grades, stages, and etiologies, including infectious and non-infectious etiologies); Schistosomiasis; Kidney cancer (all types, grades and stages); Prostate cancer (all types, grades, and stages); Prostatitis (acute and chronic); Cervical cancer (all types, grades, and stages); Uterine cancer (all types, grades, and stages); Ovarian cancer (all types, grades, and stages); Cancer of the adrenal gland (all types, grades, and stages); Cushing's disease and Cushing's syndrome; Multiple myeloma with Bence-Jones proteinuria (all stages and grades); Acute kidney injury (all types and etiologies); Acute kidney failure (all types and etiologies); Chronic kidney failure (all types, stages, and etiologies); Acute glomerulonephritis (all types and etiologies); Chronic glomerulonephritis (all types and etiologies); Focal and diffuse segmental glomerulosclerosis (all stages, grades, and etiologies, including hypertension); Membranous nephropathy (all stages, grades, and etiologies); Membranoproliferative glomerulonephritis (all stages, grades, and etiologies, including systemic lupus erythematosus); Hemolytic uremic syndrome; IgA nephropathy (all stages, grades, and etiologies); Minimal change nephropathy (all stages, grades, and etiologies); Congenital nephropathy (all stages, grades, and etiologies); Diabetic nephropathy; Protein-losing nephropathy and nephrotic syndrome (all stages, grades, and etiologies); Acute pyelonephritis (all stages, grades, and etiologies); Chronic pyelonephritis (all stages, grade, and etiologies); Lyme disease (all stages and clinical presentations); Atypical borreliosis; Myalgic Encephalomyelitis/Chronic Fatigue Syndrome (ME/CFS) (all types, stages, and etiologies); Systemic mold allergy/toxicity; Hemobartonellosis; SARS-CoV-1 (Severe Acute Respiratory Syndrome Coronavirus Disease); SARS-CoV-2 (COVID-19 Disease); and MERS-CoV-2 (Middle Eastern Respiratory Syndrome Disease).

Aspect 4 is the system of any of Aspects 1-3, wherein one or more of the chemometric analyses comprises identifying a condition of a subject by: comparing the Raman spectral data on a urine sample of the subject to a selected model; wherein the selected model is constructed from various Raman spectra of urine from individuals having and not having a specified condition; wherein the comparing of the Raman spectra of the urine sample to the selected model comprises identifying whether the urine sample is classified according to the selected model as being urine either from a subject who has or does not have the specified condition.

Aspect 5 is the system of any of Aspects 1-4, wherein the selected model is constructed from: one or more multivariate analysis techniques applied to various Raman spectra of urine from individuals having and not having the specified condition; wherein one or more of the multivariate analysis techniques involves identifying statistically significant spectral differences between the urine from the individuals having the specified condition and those not having the specified condition.

Aspect 6 is the system of any of Aspects 1-5, further comprising a component box for housing one or more components chosen from the Raman spectrometer, a laser, computer, processor, memory, motor control(s), or motor power supply.

Aspect 7 is the system of any of Aspects 1-6, wherein the component box is disposed under and as a support for one or more of the sample carousels.

Aspect 8 is the system of any of Aspects 1-7, wherein the memory has one or more reference set of Raman spectra stored thereon.

Aspect 9 is the system of any of Aspects 1-8, wherein one or more of the sample carousels is configured to hold up to 50 samples.

Aspect 10 is the system of any of Aspects 1-9, wherein the sample carousel is configured to accept vials, test tubes, specimen cups, and/or well plates.

Aspect 11 is the system of any of Aspects 1-10, wherein the computer-executable instructions are capable of controlling operation of and sequencing of the sample carousel, the Raman spectrometer and a laser in a manner such that (a) the sample carousel is capable of being rotated to present the sample in a first position, (b) then the laser is capable of interrogating the sample at the first position, and (c) then the Raman spectrometer is capable of generating Raman spectral data of the sample.

Aspect 12 is the system of any of Aspects 1-11, wherein the system is configured to test up to 400 samples per day.

Aspect 13 is the system of any of Aspects 1-12, wherein the computer-executable instructions are capable of controlling the Raman spectrometer to: administer a set number of scans per sample; apply a selected integration time; and/or administer the scans with a selected time delay between the scans.

Aspect 14 is the system of any of Aspects 1-13, wherein the system is configured to analyze liquid, solid, urine or water samples.

Aspect 15 is the system of any of Aspects 1-14, wherein the system is configured to obtain qualitative measurements.

Aspect 16 is the system of any of Aspects 1-15, wherein the system is configured to obtain quantitative measurements.

Aspect 17 is the system of any of Aspects 1-16, wherein the system is configured to analyze one or more sample using more than one excitation wavelength.

Aspect 18 is the system of any of Aspects 1-17, wherein the chemometric analyses on the Raman spectral data involves analyzing wavenumber clusters selected based on types of molecules expected relating to various pathologic features of a specified condition.

Aspect 19 is the system of any of Aspects 1-18, wherein the Raman spectrometer uses a 785 nm laser for collecting the Raman spectral data; and the chemometric analyses on the Raman spectral data involves analyzing wavenumbers in one or more of the following ranges: urea band in the range of about 1,000 to 1,005 $cm^{-1}$, 1,002 $cm^{-1}$ and/or 1,003 $cm^{-1}$ bands, uric acid at 981 $cm^{-1}$, creatinine at 680 $cm^{-1}$, collagen at 870 $cm^{-1}$, glucose at 1,071 $cm^{-1}$, 1,117 $cm^{-1}$, phosphatidylinositol (576 $cm^{-1}$), nucleic acids (721, 827, 1340 $cm^{-1}$), protein (or collagen) (817, 981, 1065, 1127, 1340 $cm^{-1}$), aromatic amino acids (827, 1004 $cm^{-1}$), cholesterol and fatty acids (702, 1297 $cm^{-1}$), monosaccharides (846 $cm^{-1}$), glycogen (1048 $cm^{-1}$), carotenoids (1417, 1518 $cm^{-1}$), 1,050-1,250 $cm^{-1}$ (lipids, carbohydrates, phosphate stretching, and C N stretching of amides and proteins, 1,590-1,750 $cm^{-1}$ (protein assignments, namely to aromatic amino acids), 669, 750, 752, 999, 1,122, 1,210, 1,444, 1,543, 1,579, 1,617 $cm^{-1}$ (heme and red blood cells), around 900 $cm^{-1}$ and from 1,200-1,400 $cm^{-1}$ (associated with tryptophan and protein, including collagen), 620 $cm^{-1}$ (related to aromatics), 880 $cm^{-1}$, 1,360 $cm^{-1}$, 1,364 $cm^{-1}$ (tryptophan), 642 $cm^{-1}$, 665 $cm^{-1}$ (related to tyrosine), and/or 1,211 $cm^{-1}$ (tyrosine and phenylalanine).

Aspect 20 is a method of identifying a condition of a subject, comprising: obtaining Raman spectra from a urine sample from a subject using the system of claim 1; comparing the Raman spectra of the urine sample to a selected model; wherein the selected model is constructed from various Raman spectra of urine from individuals having and not having a specified condition; and wherein the comparing of the Raman spectra of the urine sample to the selected model comprises identifying whether the urine sample is classified according to the selected model as being urine either from a subject who has or does not have the specified condition; optionally wherein the selected model is constructed from: one or more multivariate analysis techniques applied to various Raman spectra of urine from individuals having and not having a specified condition; wherein one or more of the multivariate analysis techniques involves identifying statistically significant spectral differences between the urine from the individuals having the specified condition and those not having the specified condition.

BRIEF DESCRIPTION OF THE DRAWINGS

The accompanying drawings illustrate certain aspects of implementations of the present disclosure, and should not be construed as limiting. Together with the written description the drawings serve to explain certain principles of the disclosure.

FIG. 14 is an illustration showing an alternative graphic user interface according to an embodiment of the invention.

FIG. 17 is an illustration showing a user interface including a progress bar indicating to a user how many samples have been scanned during an automated test of the system.

FIG. 18 is a diagram showing a user interface for a finished test run of the system.

DETAILED DESCRIPTION OF VARIOUS EMBODIMENTS OF THE INVENTION

Chronic Kidney Disease (CKD) is an illness caused by the progressive loss of renal function, and it affects roughly 30 million Americans. The culmination of CKD results in End Stage Renal Disease (ESRD), which is fatal without a kidney transplant (Senger, R. S., Kavuru, V., Sullivan, M., Gouldin, A., Lundgren, S., Merrifield, K. (2019), Spectral characteristics of urine specimens from healthy human volunteers analyzed using Raman chemometric urinalysis (Rametrix). PLoS ONE 14(9): e0222115). Because of the scarcity of transplants, most patients are left relying on dialysis, a costly treatment that puts a tremendous burden on the patient and extends their life by only about 4 years.

Fortunately, fatal CKD may be avoidable if it is diagnosed in the beginning stages of the disease progression (Senger, R. S., Sullivan, M., Gouldin, A., Lundgren, S., Merrifield, K., Steen, C., Spectral characteristics of urine from patients with end-stage kidney disease analyzed using Raman Chemometric Urinalysis (Rametrix) PLoS ONE 15(1): e0227281, 2020). RAMETRIX™ is a novel public health screening technology based on Raman spectroscopy and chemometric analyses. It has been shown to detect the early signs of CKD in urine, and it has been used to diagnose and prevent ESRD (Senger, 2020).

The inventors have leveraged this valuable technology to create an efficient screening tool for use in practical settings such as hospitals and dialysis centers that reduces technician time as compared with analyzing urine specimens manually and increases processing capacity with a high-throughput solution.

In embodiments, the present invention comprises a large-scale automated processor system for performing RAMETRIX™ urine analyses. Normal urine contains over 2000 discrete chemical entities. The number of chemical entities, the types of molecules, and the concentrations of the different components may vary widely in the urine of individuals with diseases. Systems which specialize in urinalysis, are typically better equipped to spot these differences. In embodiments, the system requires minimal user interaction and is easily implemented in a lab or clinical setting. The system can include software code in Python to achieve automation of the AutoScanner to complete sample identification, device loading, and device operation that corresponds with the automated features of the device. In embodiments, the system comprises a graphical user interface (GUI) to provide communication between the operator and the AutoScanner in an intuitive way. Overall, the AutoScanner solves the problem of labor-intensive, small-scale processing by providing a way to scan up to 200 samples or more per day with minimal user interaction in a practical setting such as a hospital or dialysis center.

Figure 1:
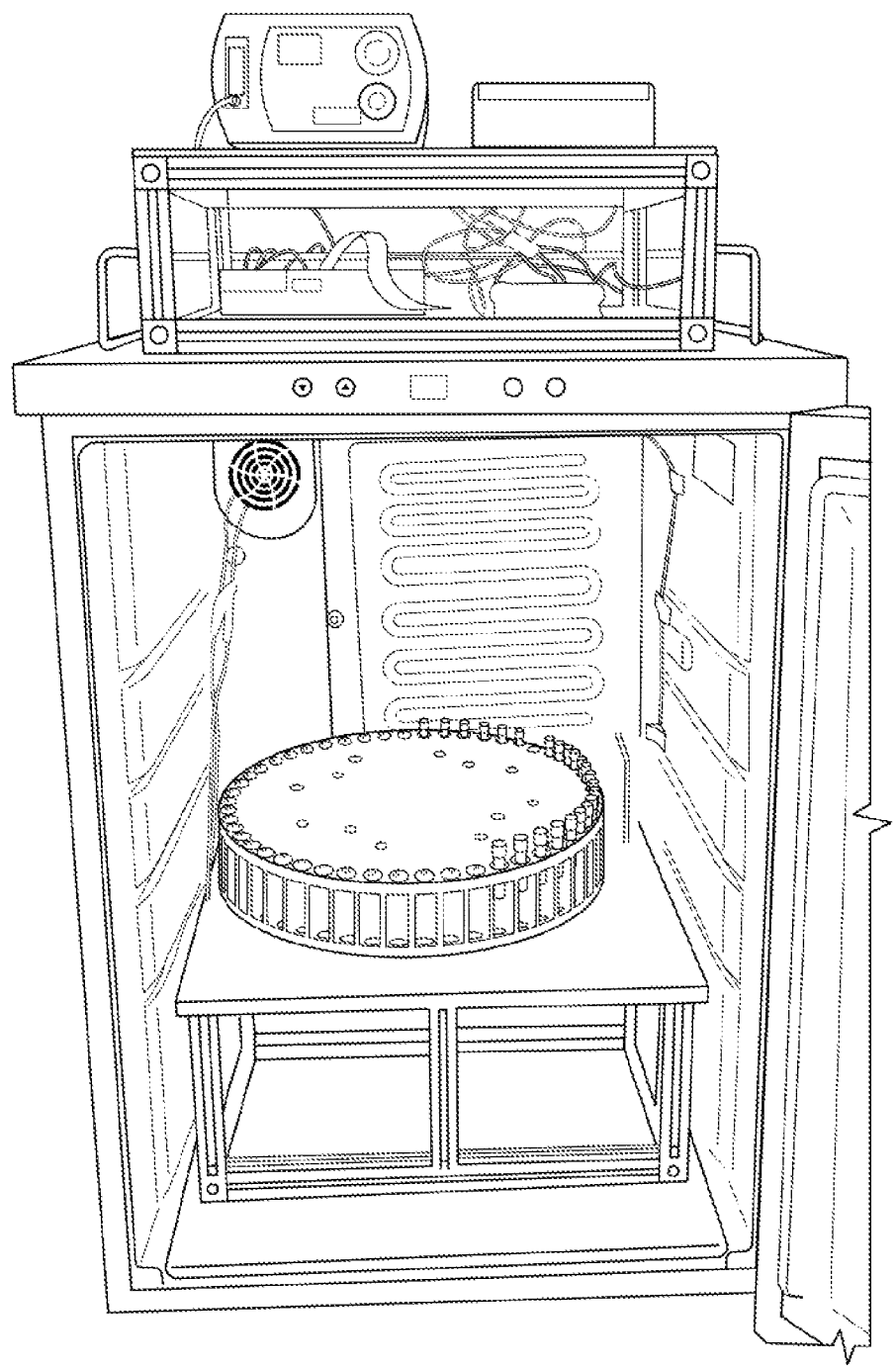
FIG. 1 is a photograph showing the inside of the system according to an embodiment of the invention.

FIG. 1 shows an embodiment of the invention which includes an aluminum scaffold holding an aluminum carousel capable of holding up to at least 50 urine samples. The system features controlled rotation of a nema 34 stepper motor (initiated by a RaspberryPi) with separate stimulus of the Raman laser to collect data. The motor is connected to a driver that is compatible with the nema 34 stepper motor which is also connected to a 24V DC power supply.

In embodiments, the AutoScanner system includes software that controls the individual component pieces. In an embodiment, the entire system can be controlled through a laptop-RaspberryPi system. This coding essentially alternates the rotation of the carousel motor, the firing of the Raman laser, and the processing of the acquired data for each sample. In embodiments, processing of the acquired data can be performed contemporaneously with any of the other functions of the system, such that while the carousel is moving to the next sample or while the Raman laser is firing on a sample, the data processing can be performed on that sample and/or on one or more or multiple previous samples. In embodiments, the processing of the acquired data involves performing one or more chemometric analyses on the acquired Raman spectral data, such as by way of the RAMETRIX™ software. In a chemometric analysis, Raman spectra are treated as "spectral fingerprints," and multivariate statistical tools discover unique features and similarities among spectra.

In embodiments, the system comprises a graphical user interface (GUI) for the AutoScanner. The GUI is a web-based system that is housed on a laptop and connected to the system through the RaspberryPi. The GUI prompts the user in the set up and running of the device and gives the user the ability to adjust the settings of each run as necessary. Once the run is initiated, the GUI communicates with the RaspberryPi to control the function of the AutoScanner.

Figure 2:
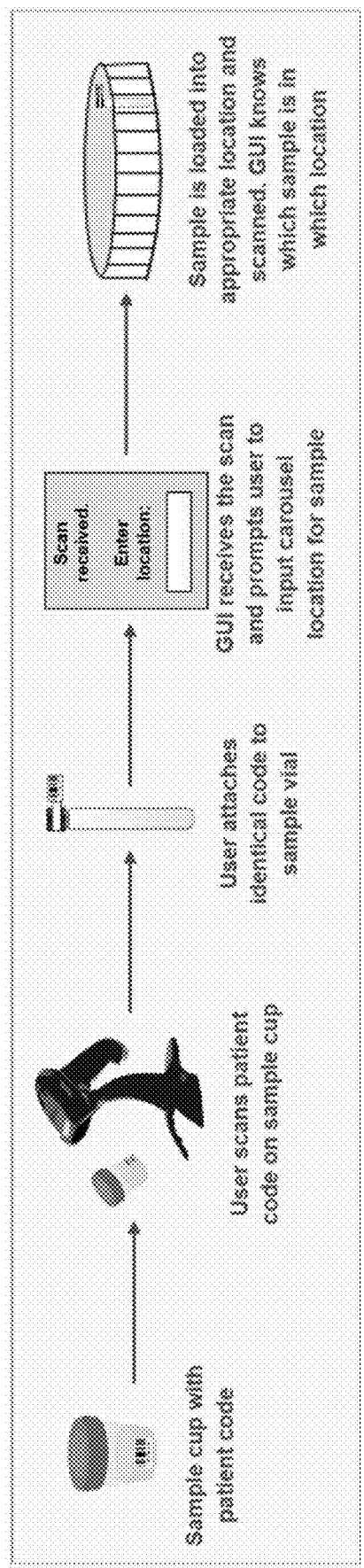
FIG. 2 is an illustration showing the identification and loading process a user follows when inserting samples into the system according to an embodiment of the invention.

In embodiments, the system includes an automated process for sample identification and carousel loading. In order to ensure appropriate use of the AutoScanner, a standard operating procedure (SOP) was established for easy user training and system implementation. A large part of this procedure is sample identification. Since each biological sample needs to be transferred from the patient, to their specimen cup, to a sample vial, and then into the AutoScanner, it is possible for errors such as sample swapping, mislabeling, or misidentification that would prevent accurate scanning and data pairing between a patient and their results. Thus, in an embodiment the system is compatible with a sample identification method based on barcode labeling of specimen cups that is common in hospitals and clinics. As shown in FIG. 2, the user will identify and load each sample into the carousel individually to minimize error. This process requires GUI prompts, a barcode scanner, and a label printer, and—when coupled with the SOP instructions—provides a simple method for sample identification while maintaining patient privacy.

In embodiments, the carousel is configured to accept sample containers from the top and/or side. In embodiments, the sample containers are vials, test tubes, or well plates. In embodiments, the sample containers are glass and/or plastic.

In other embodiments, the system is compatible with patient specimen cups, eliminating the need to transfer samples to vials. A barcode is placed directly on the specimen cup to further minimize sample swapping, mislabeling, and/or misidentification.

Figure 3:
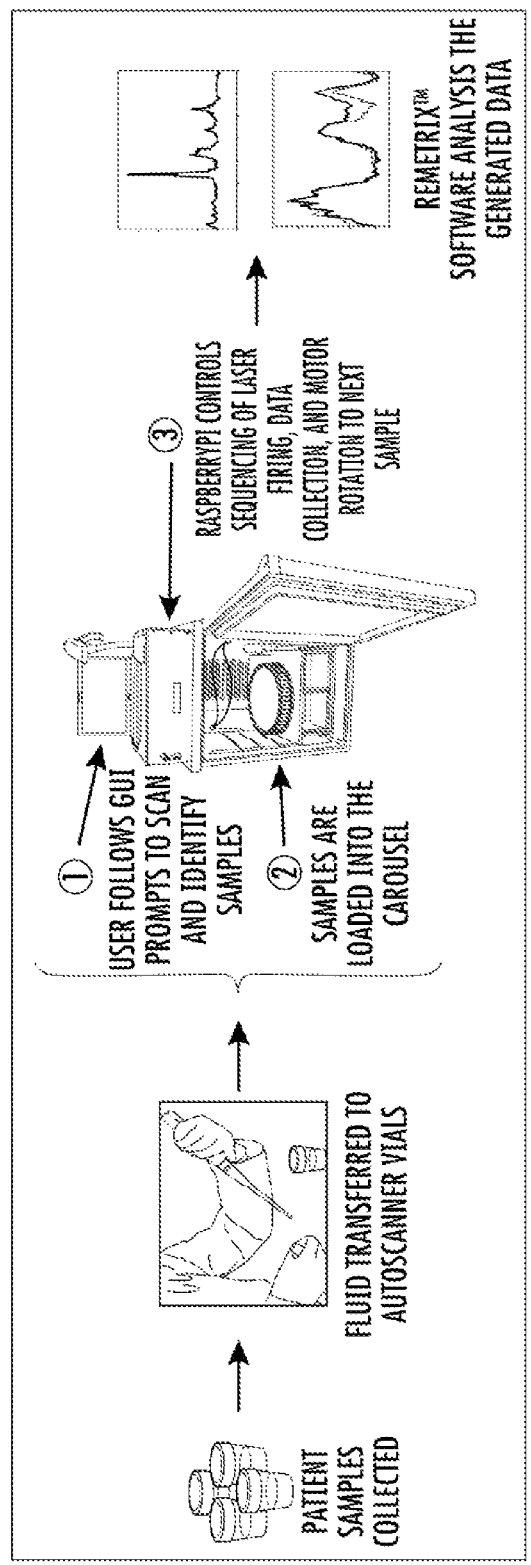
FIG. 3 is an illustration showing the full sample analysis sequence according to an embodiment of the invention.

The function of the AutoScanner and its related processes are shown in FIG. 3. Once the patient samples are received, the user transfers the fluid into sample vials and follows the identification method as prompted by the GUI (1). Once the samples are loaded in the identification and initialization stage (1-2), the run is started on the GUI, and the RaspberryPi takes control (3). The hard-code scans each sample with the parameters specified by the user (in the GUI) and uploads the data back onto the laptop/computer before triggering the motor rotation to the next sample. This process repeats for each sample in the carousel. In embodiments, the system is capable of rotating in either a clockwise or counterclockwise direction or both to advance to the next sample or to re-visit a previous sample/position on the carousel. Finally, once the run is completed, the data on the laptop/computer can be accessed and analyzed with the RAMETRIX™ software to determine significance.

Figure 4:
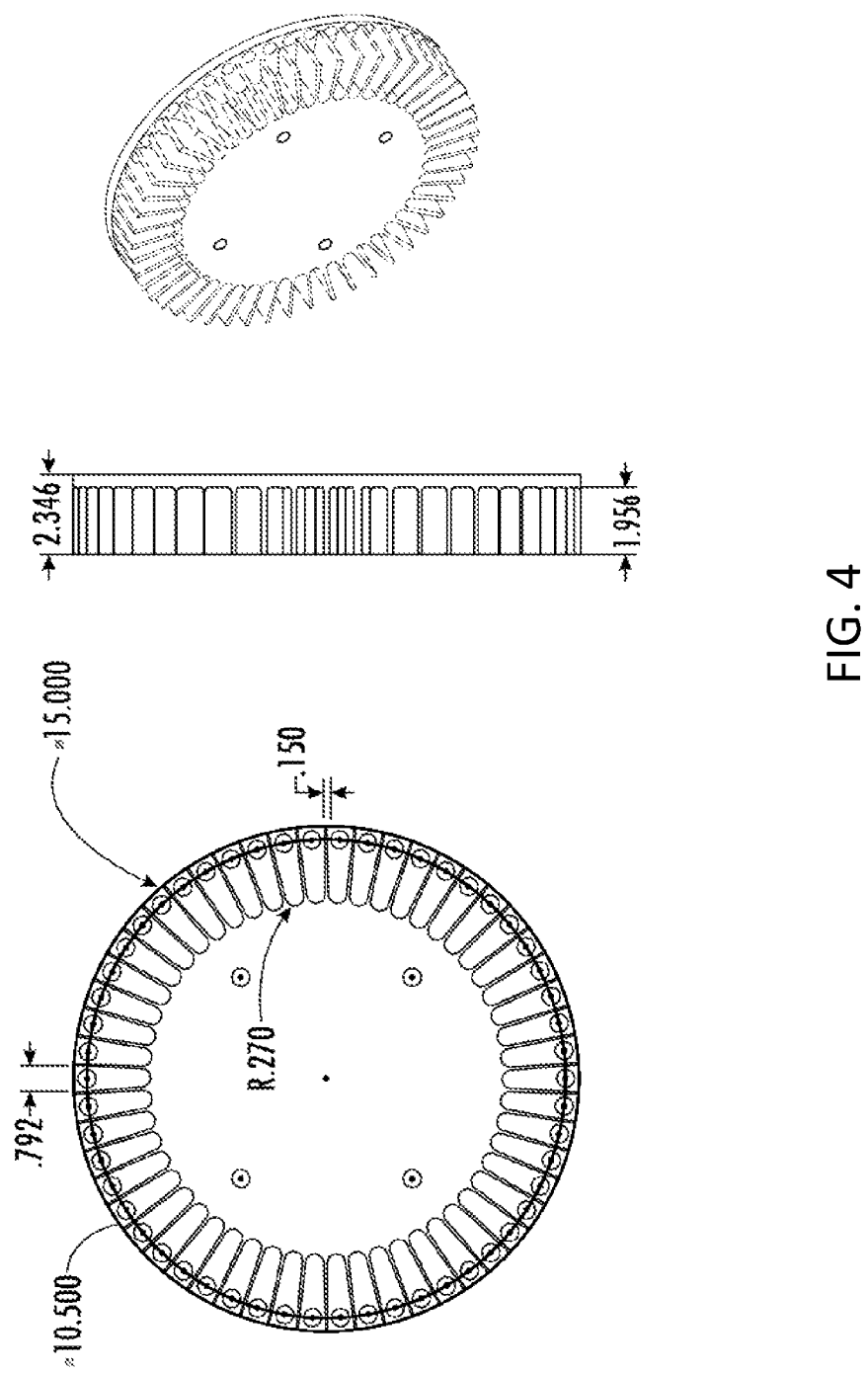
FIG. 4 is an illustration showing the specifications for the sample carousel according to an embodiment of the invention.
Figure 5:
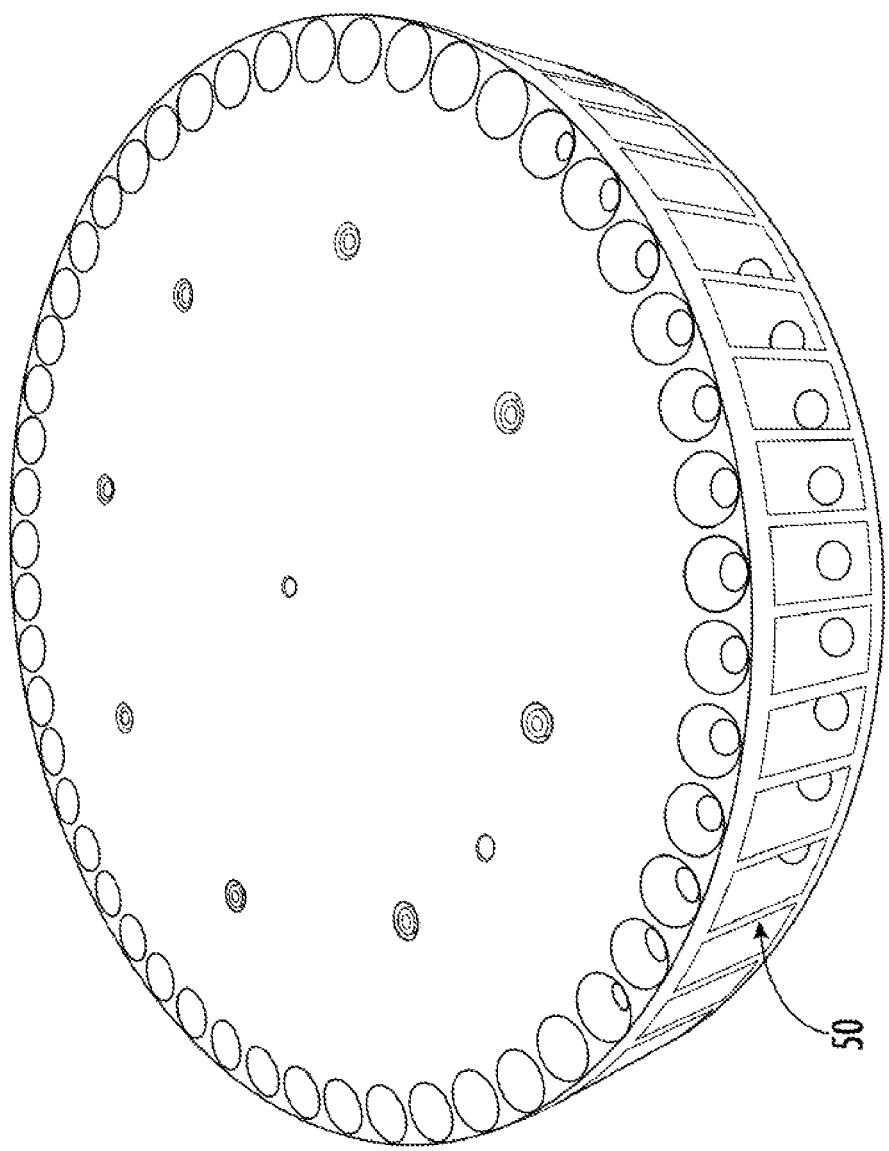
FIG. 5 is a photograph of a sample carousel according to embodiments.
Figure 6:
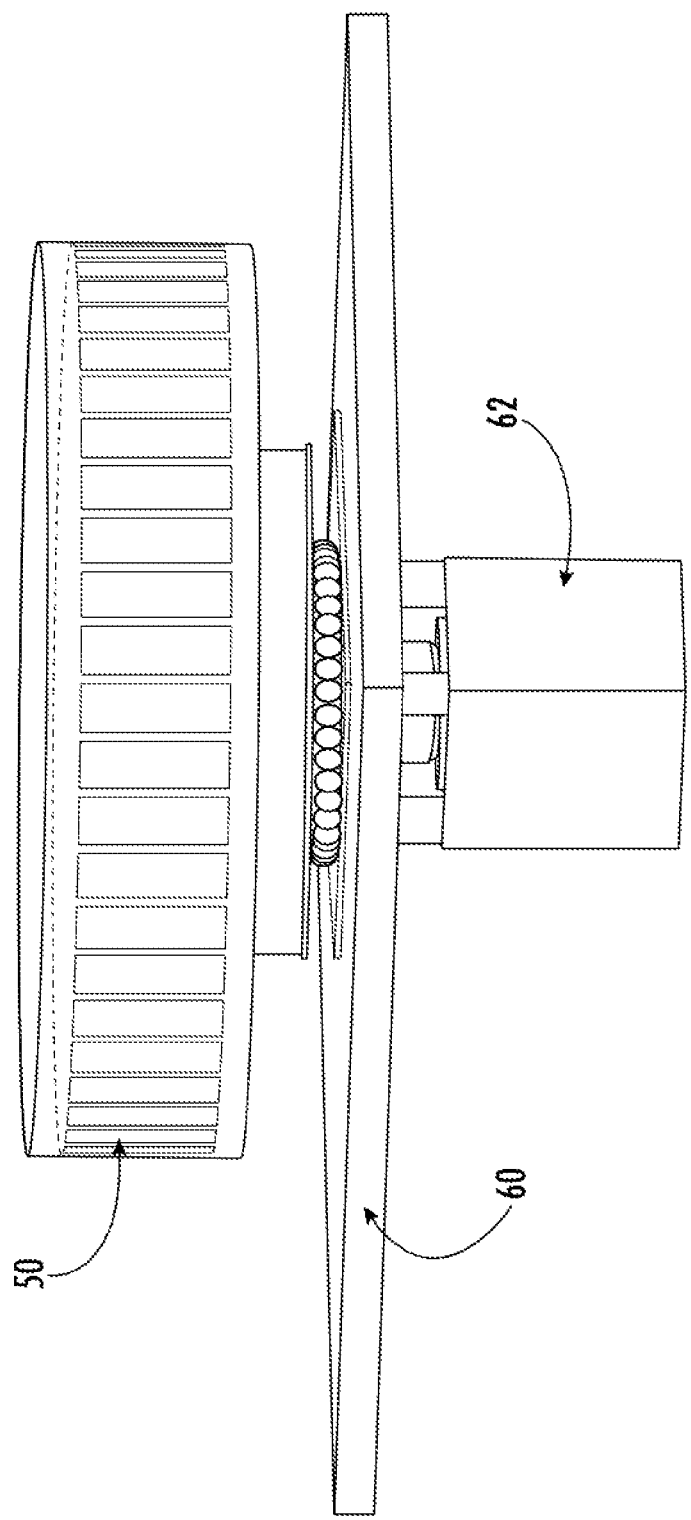
FIG. 6 is an illustration showing the sample carousel and platform assembly according to an embodiment of the invention.
Figure 7:
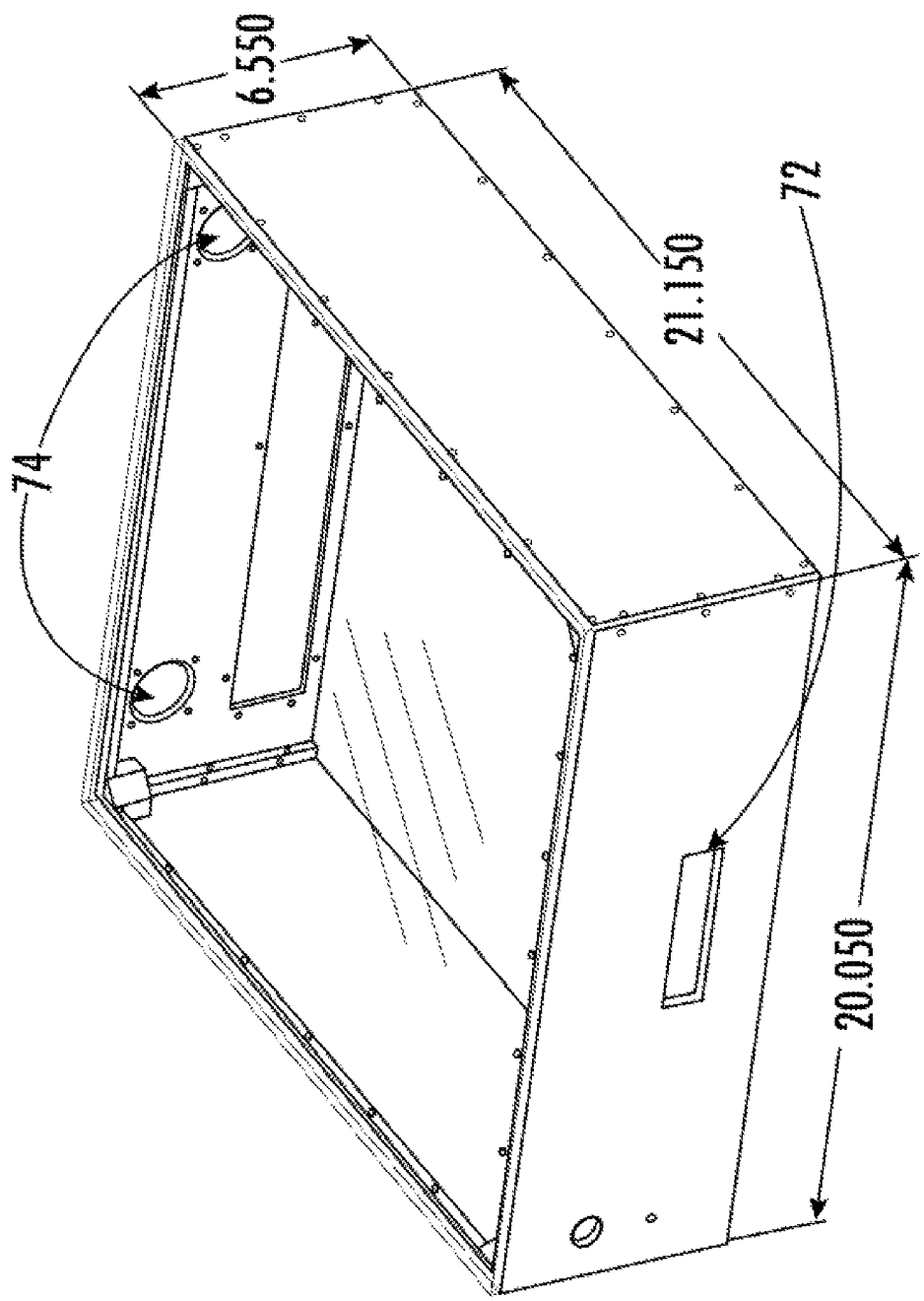
FIG. 7 is an illustration of the component box dimensions according to an embodiment of the invention.

In embodiments, each sample is loaded into a carousel (FIGS. 4-6). The carousel comprises sample vial holders 50 located about its perimeter. In embodiments, the carousel can be configured to have multiple rows of sample vial holders disposed around the circumference of the carousel. In embodiments, the carousel comprises up to 200 sample vial holders, such as 10, 25, 50, 75, 100, 150, or 175 sample vial holders. In embodiments, the carousel rests on a platform 60. Beneath the platform 60 is a motor housing 62 which holds the motor (not shown).

Figure 8:
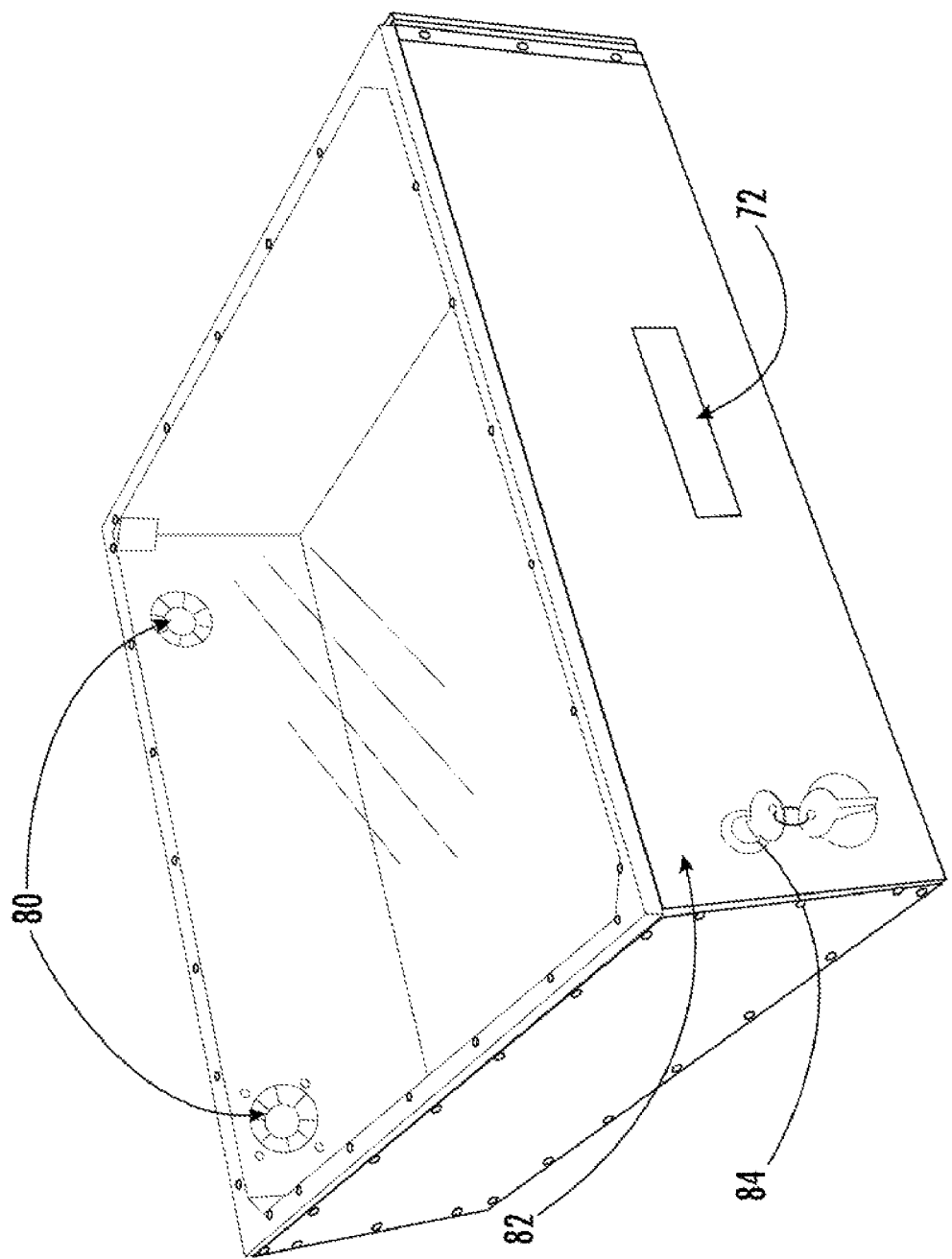
FIG. 8 is a photograph showing a front perspective view of the component box according to an embodiment of the invention.
Figure 9:
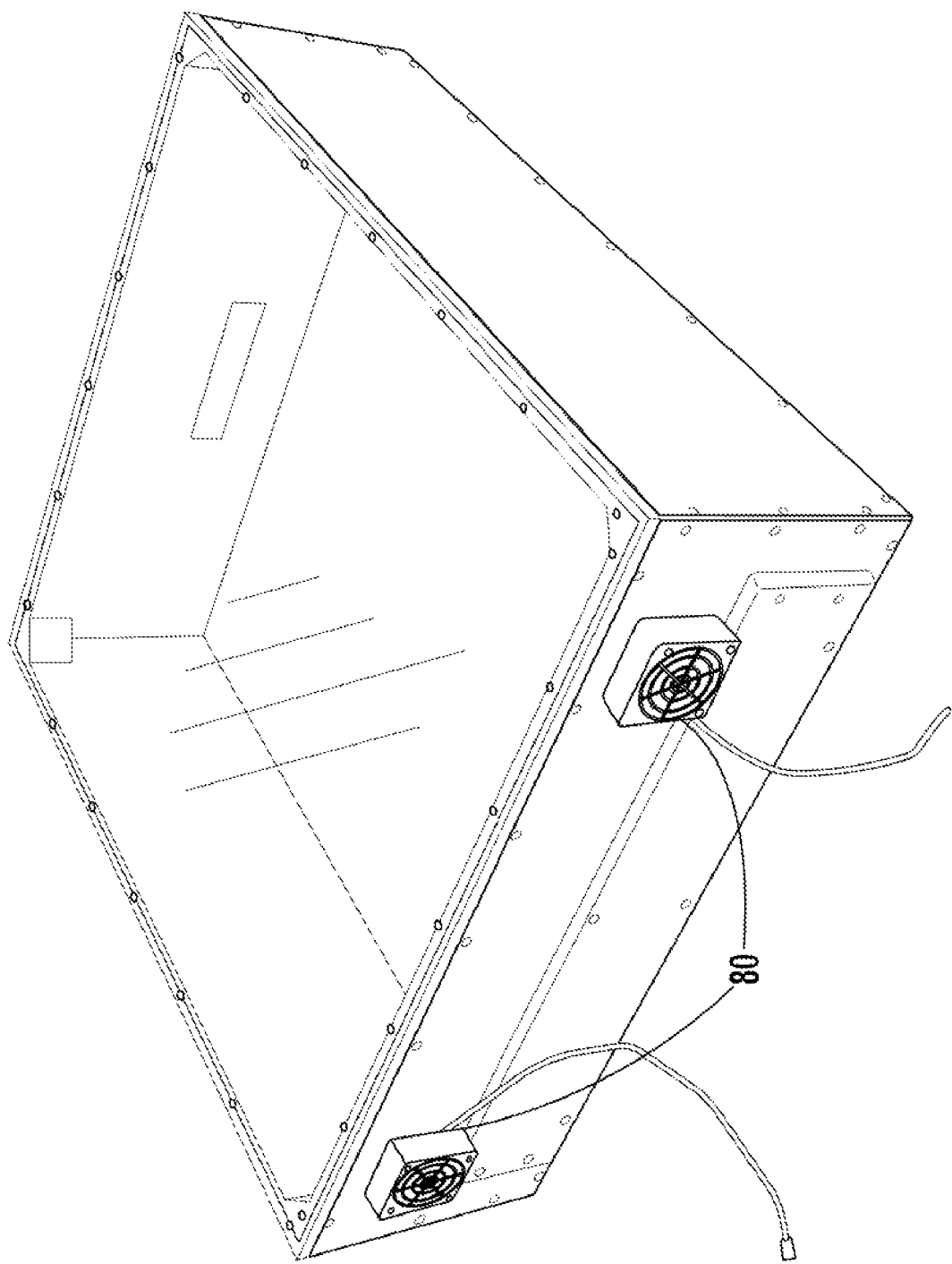
FIG. 9 is a photograph showing a back perspective view of the component box according to an embodiment of the invention.
Figure 10:
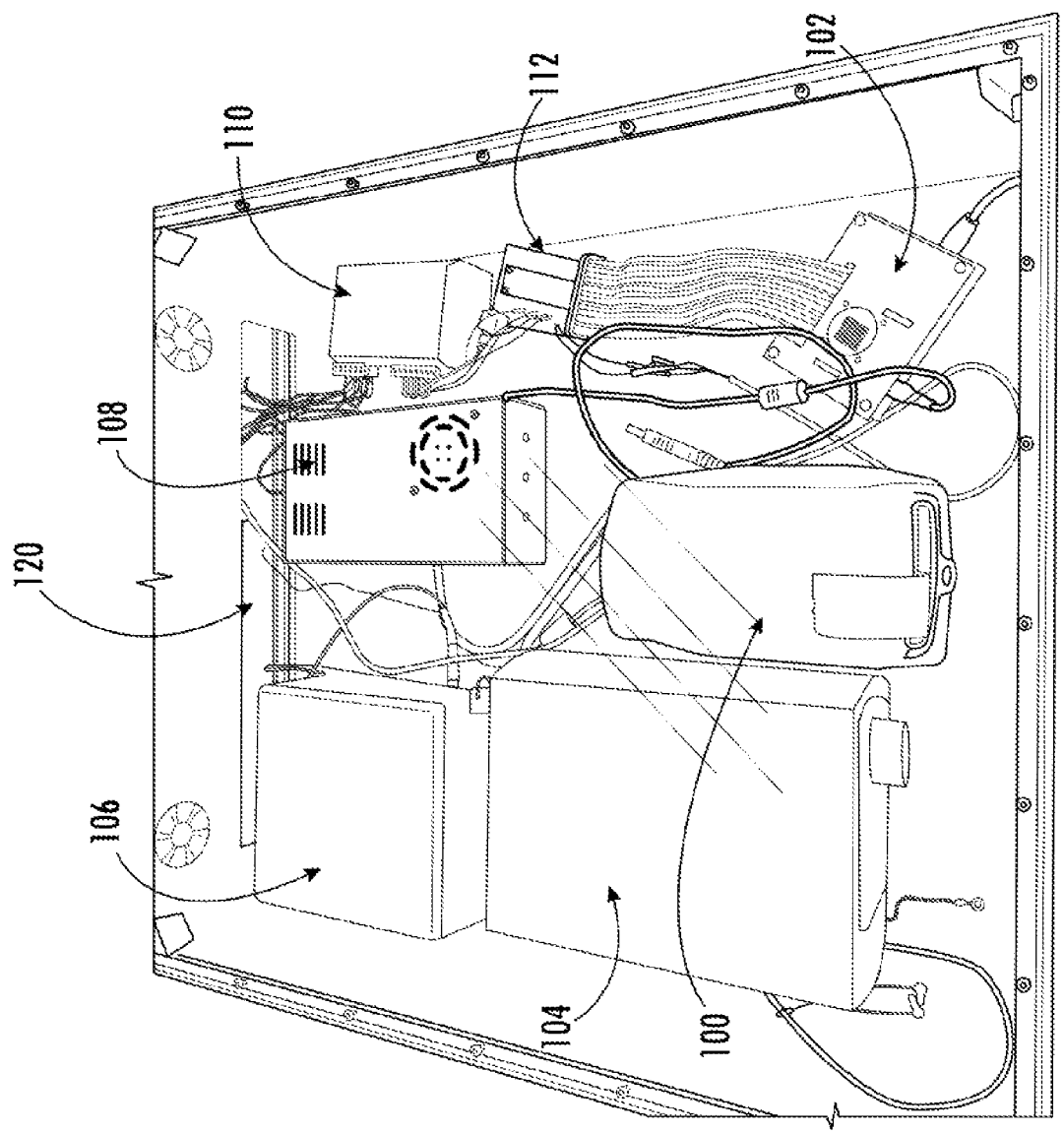
FIG. 10 is a photograph showing the component box housing components according to an embodiment of the invention.

In embodiments, the system further includes a component box (FIGS. 7-10). The component box provides an organized space for many of the components of the AutoScanner. The slot 72 on the front allows the sample labels to be easily accessed and removed from the label maker 100 as they are dispensed. On the back of the component box (FIG. 7), two holes 74 are present and configured to house two fans 80 to help regulate the temperature inside the component box and ensure the safety of the electrical components. FIG. 8 shows the front of the box, which features a door 82 that opens and can be secured with a lock and key 84, allowing the user to have easy access to the most important components of the AutoScanner. FIG. 10 shows the components housed in the component box such as the label maker 100, the RaspberryPi 102, the laser 104, the Raman spectrometer 106, the carousel motor power supply 108, the motor control 110, and the breadboard 112. Additionally, the slot 120 near the bottom of the box allows the cords to exit the compartment in a simple fashion. Finally, the top of the box is clear for easy visualization of all of the components, and it can be removed in the event that the components need to be altered or adjusted.

Figure 11:
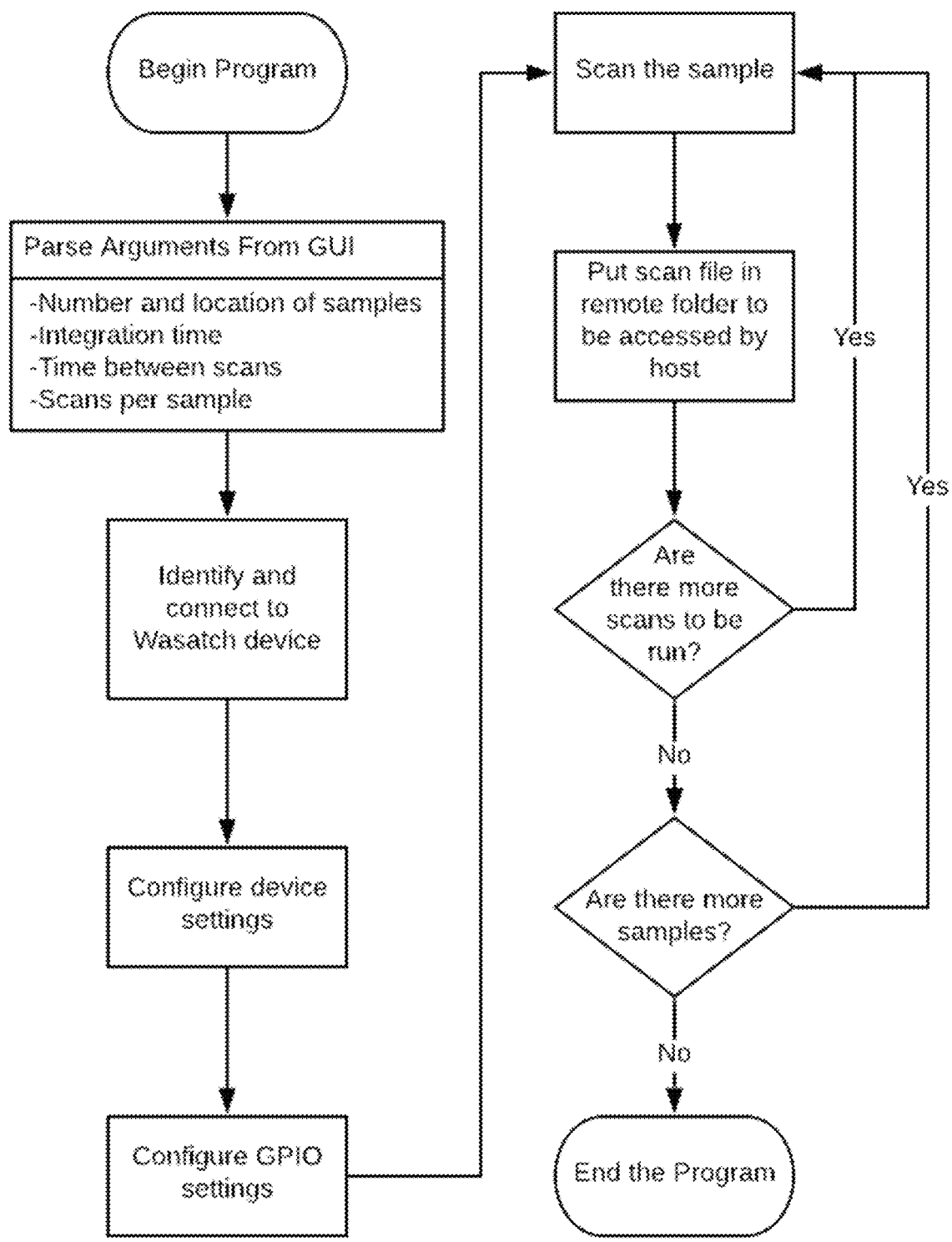
FIG. 11 is an illustration showing the code controlling the function of the system according to an embodiment of the invention.

The flowchart shown in FIG. 11 provides the basic sequence of the Python instructions. When a user initiates the program, the system will parse arguments from the graphical user interface (GUI), including parameters input by the user such as the number and locations of the samples, the integration time, the time between scans, and the number of scans per sample. Next the program will identify and connect to the Wasatch device (Raman spectrometer 106) and configure the device settings. The program will then configure the general-purpose input/output pins of the RaspberryPi 102. The program will use the Raman spectrometer 106 and laser 104 to scan the sample, then put the scan file into a remote folder which can be accessed by the user. If additional scans are to be performed, the program will repeat the scanning and archiving of data until there are no more scans to be performed. Next the program will determine if there are more samples to be tested. If there are additional samples, the scanning steps will be repeated for each sample. If no more samples are remaining, the program will end.

Figure 13:
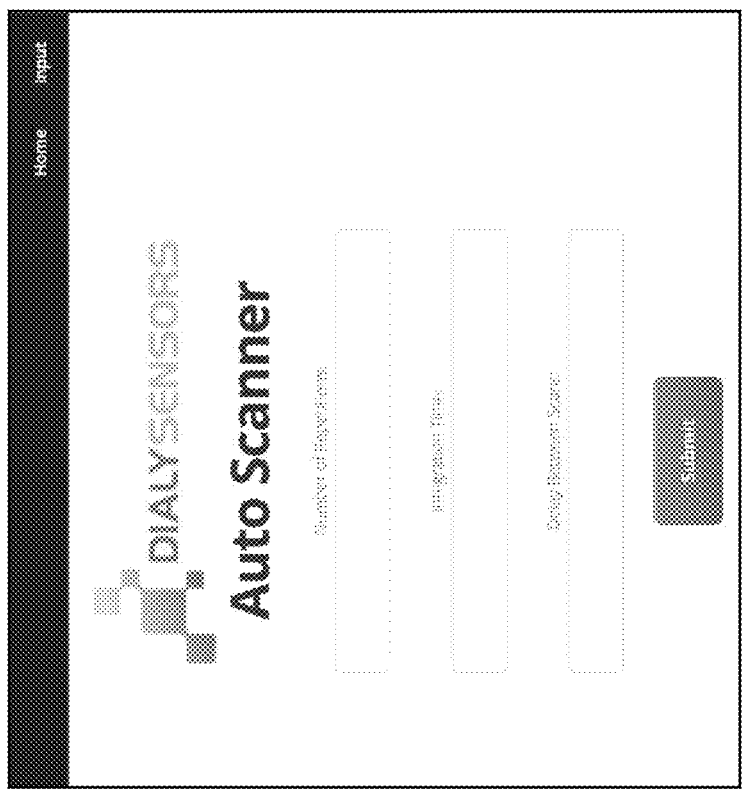
FIG. 13 is an illustration showing the input page of the graphic user interface according to an embodiment of the invention.
Figure 12:
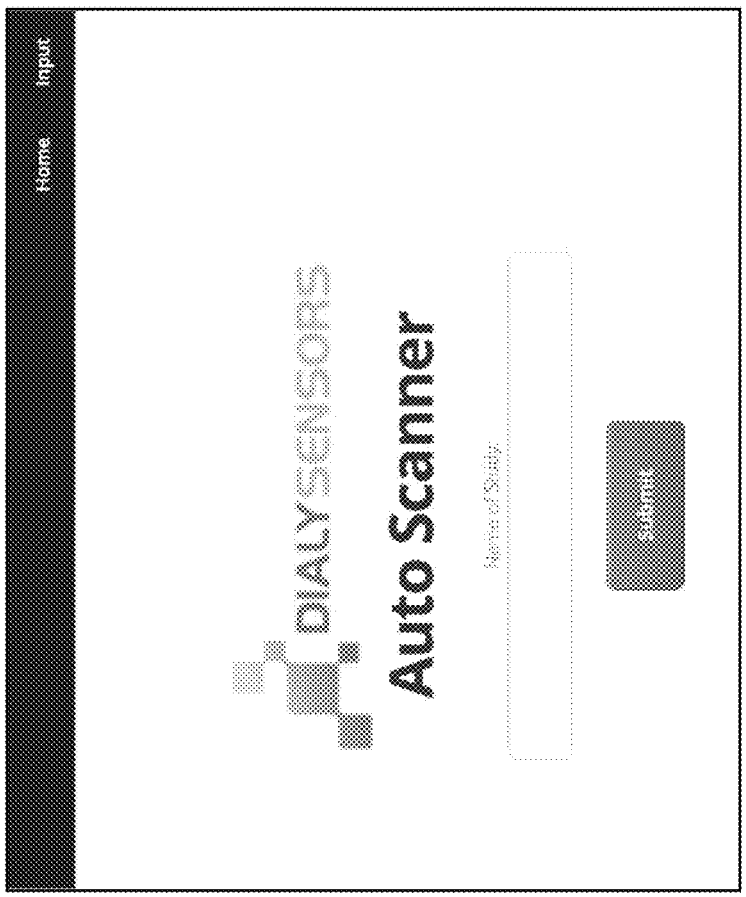
FIG. 12 is an illustration showing the homepage of the graphic user interface according to an embodiment of the invention.
Figure 14:
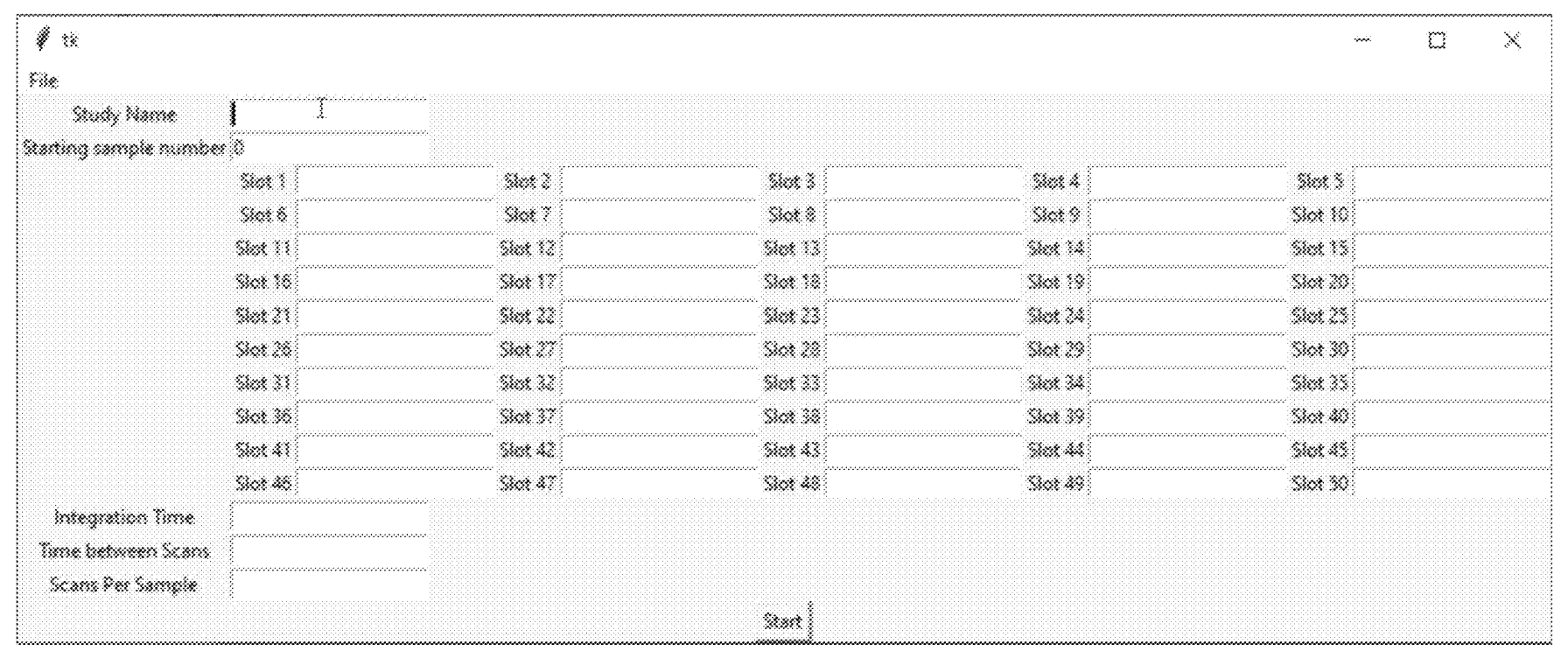

Examples of the GUI are shown in FIGS. 12-13. On the homepage of the GUI (FIG. 12), the user inputs the number of samples, which triggers the GUI to expect the same number of barcode entries (for the sample identification process) as each sample is scanned. After the user submits these entries, they are directed to the next page (FIG. 13) where they are prompted to input the desired number of scans per sample (repetitions), the integration time, the delay between scans, and the depository location for the finished data files. For security purposes, the user must type the file path for the files to be deposited instead of selecting it from the computer. After clicking "Submit" again, if the submission is successful, the user will be presented with a success message; if not, they will be presented with an error. An alternative GUI developed in Python is shown in FIG. 14, which allows for the same information to be entered/presented but arranged in a different way.

Figure 15:
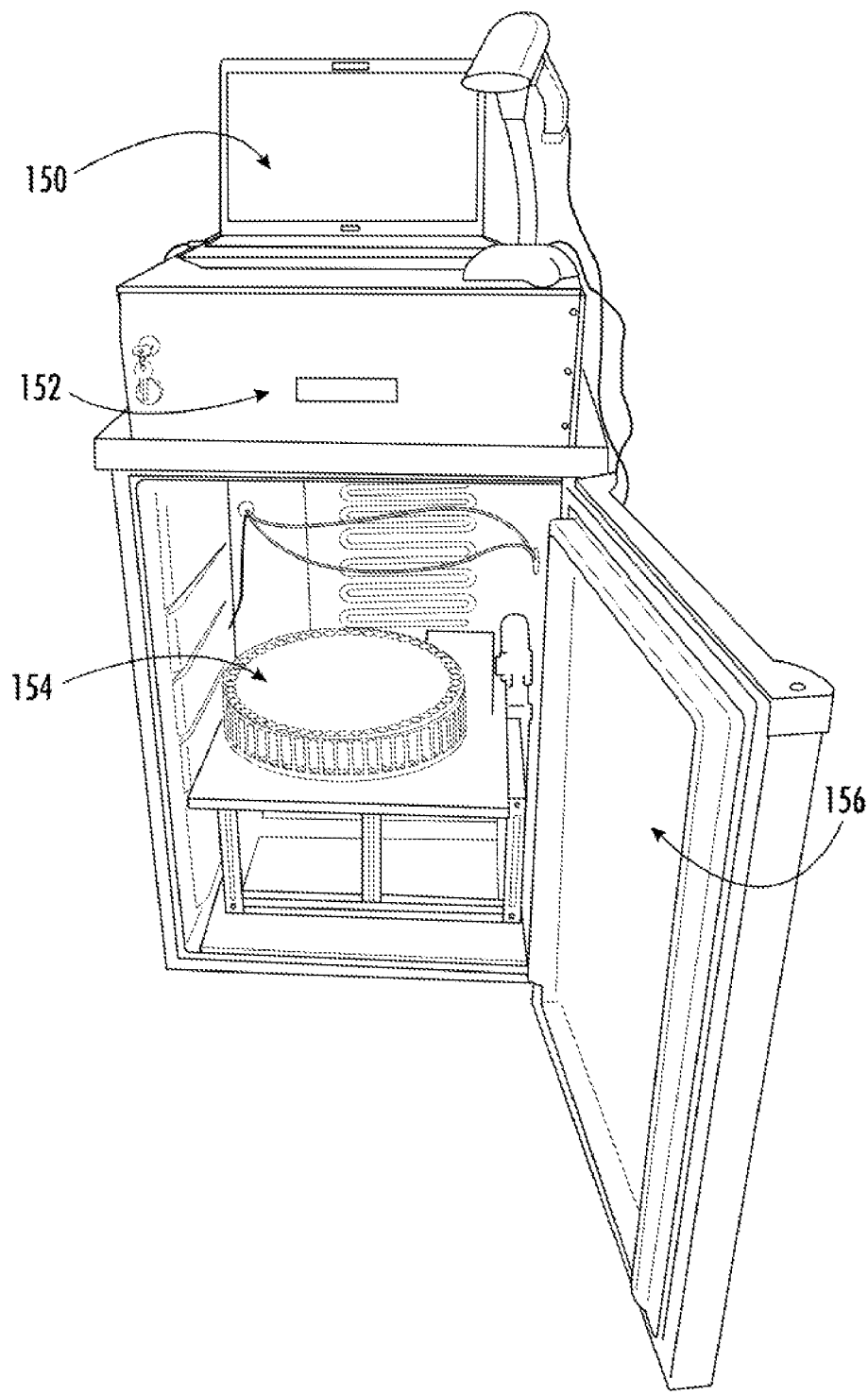
FIG. 15 is a photograph showing an assembled system according to embodiments.

An embodiment of the system comprising all components described is shown in FIG. 15. The system comprises a laptop 150 (or other computer), component box 152, carousel 154, and carousel housing 156.

In embodiments, the system is configured to connect to a user's existing Raman spectrometer. In some embodiments, the system is configured to include a handheld Raman spectrometer. Examples of handheld Raman spectrometers are described in U.S. Pat. Nos. 7,505,128; 7,524,671; 7,651, 851 and 8,699,020, and U.S. Patent Application Publication No. 20140052386 A1, which are incorporated by reference herein in their entireties.

The Raman spectrometer may 106 be a benchtop spectrometer. Examples of benchtop Raman spectrometers include those described in U.S. Pat. Nos. 5,786,893; 5,534, 997; and 6,100,975. The fiber optic probe may have a dichroic mirror, which separates Raman scattered light from laser light by reflecting laser light and allowing Raman-scattered wavelengths to pass. Laser light and Raman scattered light may be transmitted through separate fibers (collection fiber(s) and excitation fiber(s)). Filters may be placed before the fibers for blocking undesirable wavelengths, such as a long pass filter placed before the collection fiber (blocks reflected laser light) and a band-pass filter placed before the excitation fiber (blocks Raman scattered light). The fiber optic probe may include one or more lenses for focusing the light onto the sample or onto the fibers. An example of such a fiber optic probe is the RAMANPROBE™, described in U.S. Pat. No. 5,112,127. Another example is a Raman fiber optic probe embedded in a microfluidic device, described in U.S. Pat. No. 8,638,431. Another example is a dual and multi-wavelength Raman sampling probe described in U.S. Patent Application Publication No. 20120099102.

The laser 104 may emit monochromatic light at any wavelength, including far infrared, mid infrared, infrared, near infrared, visible light, ultra-violet, and extreme-ultra-violet, or at multiple wavelengths. In embodiments, the Raman spectra are collected using a 785 nm laser, such as an Agiltron (Woburn, MA) PeakSeeker™ PRO-785 Raman spectrometer utilizing a 100 mW, 785 nm laser with spot size 0.1-0.2 mm, with an integration time of up to 30 seconds, such as 10 seconds, 15 seconds, or 20 seconds. Embodiments can include using a 785 nm (30 mW) laser excitation for 30 s. The choice of wavelength may depend on the target molecule one wishes to measure. For example, for visible wavelengths such as blue or green can be good for inorganic molecules, while ultraviolet wavelengths may be optimal for measuring biomolecules such as proteins, RNA, and DNA as these tend to absorb UV radiation. In addition, embodiments may include multiple lasers to represent multiple wavelengths.

For example, distinguishing features of variability in Raman spectra of urine and the wavenumbers that give rise to the separations indicating a difference between having and not having chronic kidney disease is one or more or all of the urea band in the range of about 1,000 to 1,005 cm$^{-1}$, such as at 1,002 cm$^{-1}$, 1,003 cm$^{-1}$, uric acid at 981 cm$^{-1}$, creatinine at 680 cm$^{-1}$, collagen at 870 cm$^{-1}$, glucose at 1,071 cm$^{-1}$; 1,117 cm$^{-1}$; and/or others, for example, when the Raman spectra are collected using a 785 nm laser.

Distinguishing features of variability in Raman spectra of urine and the wavenumbers that give rise to the separations indicating a difference between having and not having bladder cancer (BCA) occur at, for example, one or more or all of phosphatidylinositol (576 cm$^{-1}$), nucleic acids (721, 827, and 1340 cm$^{-1}$), protein (particularly collagen) (817, 981, 1065, 1127, and 1340 cm$^{-1}$), and aromatic amino acids (827 and 1004 cm$^{-1}$), cholesterol and fatty acids (702 and 1297 cm$^{-1}$), monosaccharides (846 cm$^{-1}$), glycogen (1048 cm$^{-1}$), and/or carotenoids (1417 and 1518 cm$^{-1}$), for example, when the Raman spectra are collected using a 785 nm laser.

Distinguishing features of variability in Raman spectra of urine and the wavenumbers that give rise to the separations indicating a difference between having and not having hematuria occur at, for example, one or more or all of 1,050-1,250 cm$^{-1}$ (lipids, carbohydrates, phosphate stretching, and C-N stretching of amides and proteins (among others); 1,590-1,750 cm$^{-1}$ (protein assignments, namely to aromatic amino acids); and/or 669, 750, 752, 999, 1,122, 1,210, 1,444, 1,543, 1,579, 1,617 cm$^{-1}$ (heme and red blood cells), for example, when the Raman spectra are collected using a 785 nm laser.

Distinguishing features of variability in Raman spectra of urine and the wavenumbers that give rise to the separations indicating a difference between having and not having Lyme disease occur at, for example, one or more or all of the 1,000 to 1,005 cm$^{-1}$ bands, such as at the 1,002 cm$^{-1}$ and/or 1,003 cm$^{-1}$ bands (representative of urea); around 900 cm$^{-1}$ and from 1,200-1,400 cm$^{-1}$ (all commonly associated with tryptophan and protein, including collagen); 620 cm$^{-1}$ (related to aromatics); 880 cm$^{-1}$ (tryptophan); 1,360 cm$^{-1}$ (tryptophan); 642 cm$^{-1}$, 665 cm$^{-1}$ (related to tyrosine); 880 cm$^{-1}$ (tryptophan); 1,211 cm$^{-1}$ (tyrosine and phenylalanine); and/or 1,364 cm$^{-1}$ (tryptophan), for example, when the Raman spectra are collected using a 785 nm laser.

Further, for example, distinguishing features of variability in Raman spectra of urine and the wavenumbers that give rise to the separations indicating a difference between having and not having ME/CFS occur at, for example, one or more or all of the 1,000 to 1,005 cm$^{-1}$ bands, such as at the 1,002 cm$^{-1}$ and/or 1,003 cm$^{-1}$ bands (representative of urea); around 900 cm$^{-1}$ and from 1,200-1,400 cm$^{-1}$ (all commonly associated with tryptophan and protein, including collagen), for example, when the Raman spectra are collected using a 785 nm laser.

Key wavenumber clusters can be selected based on interpretation of known pathologic features of a specified condition that may affect the types of molecules expected, such as selecting a set of key wavenumbers associated with a patient that is positive for hypertension and diabetes (HT/DM+) or selecting a set of key wavenumbers associated with a patient that is negative (HT/DM−).

In embodiments, the Raman spectrometer spot size is set by a user. The spot size can be up to about 5 mm by 5 mm, such as 1 mm by 1 mm, 2 mm by 2 mm, 3 mm by 3 mm, or 4 mm by 4 mm. In embodiments, the spot size is less than 1 mm by 1 mm, such as about 0.5 µm by 0.5 µm, 1 µm by 1 µm, 10 µm by 10 µm, 100 µm by 100 µm, or 500 µm by 500 µm. In embodiments, a user can input a desired laser excitation wavelength based on the analyte of interest within a sample. Surface-enhanced Raman scattering (SERS) can also be used. In embodiments, the system is capable of analyzing samples with volumes as low as about 1 µL.

In embodiments, the system computer comprises a memory capable of storing patient data. In some embodiments, the memory also stores one or more reference data sets.

Any method or algorithm described herein can be embodied in software or set of computer-executable instructions capable of being run on a computing device or devices. The computing device or devices can include one or more processor (CPU) and a computer memory. The computer memory can be or include a non-transitory computer storage media such as RAM which stores the set of computer-executable (also known herein as computer readable) instructions (software) for instructing the processor(s) to carry out any of the algorithms, methods, or routines described in this disclosure. As used in the context of this disclosure, a non-transitory computer-readable medium (or media) can include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM. The computer-readable instructions can be programmed in any suitable programming language, including JavaScript, C, C#, C++, Java, Python, Perl, Ruby, Swift, Visual Basic, and Objective C. Embodiments of the invention also include a non-transitory computer readable storage medium having any of the computer-executable instructions described herein.

A skilled artisan will further appreciate, in light of this disclosure, how the invention can be implemented, in addition to software and hardware, using one or more firmware. As such, embodiments of the invention can be implemented in a system which includes any combination of software, hardware, or firmware. In the context of this specification, the term "firmware" can include any software programmed onto the computing device, such as a device's nonvolatile memory. Thus, systems of the invention can also include, alternatively or in addition to the computer-executable instructions, various firmware modules configured to perform the algorithms of the invention.

According to embodiments, the computing device or devices can include a mainframe computer, web server, database server, desktop computer, laptop, tablet, netbook, notebook, personal digital assistant (PDA), gaming console, e-reader, smartphone, or smartwatch, which may include features such as a processor, memory, hard drive, graphics processing unit (GPU), and input/output devices such as display, keyboard, and mouse or trackpad (depending on the device). Embodiments can also provide a graphical user interface made available on one or more client computers. The graphical user interface can allow a user on a client computer remote access to the method or algorithm.

Additional embodiments of the invention can include a networked computer system for carrying out one or more methods of the invention. The computer system can include one or more computing devices which can include a processor for executing computer-executable instructions, one or more databases, a user interface, and a set of instructions (e.g. software) for carrying out one or more methods of the invention. According to other embodiments, the computing device or devices can be connected to a network through any suitable network protocol such as IP, TCP/IP, UDP, or ICMP, such as in a client-server configuration and one or more database servers. The network can use any suitable network protocol and can be any suitable wired or wireless network including any local area network, wide area network, Internet network, telecommunications network, Wi-Fi enabled network, or Bluetooth enabled network.

The following Examples are illustrative and should not be interpreted to limit the scope of the claimed subject matter.

EXAMPLE 1

In order to verify that the complete automation of the device had been achieved, a continuous test of the system was performed. Six samples were scanned without interruption in the AutoScanner system: urea in water (100 g/L), tap water, acetic acid in water (5%), ethanol (100%), vodka, and bourbon. Each sample was assigned a unique barcode and carousel slot location that auto-filled into the GUI when scanned by the barcode scanner.

Figure 16:
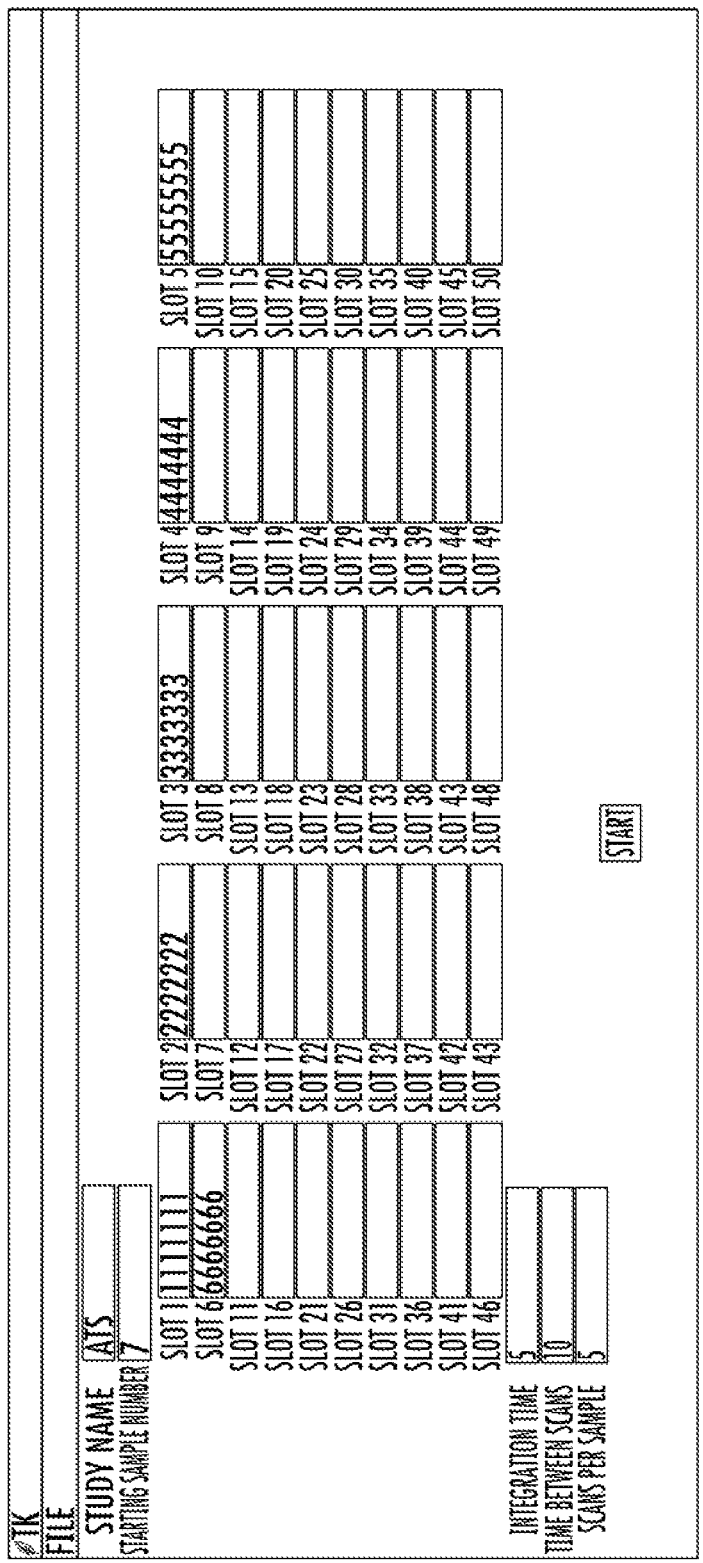
FIG. 16 is an illustration showing a user interface with the input values for a six-sample automated test of the system.

The laser parameters were adjusted to 5 second integration time, 10 second delay between scans, and 5 scans per sample. All details are pictured in the GUI (FIG. 16). In embodiments, the laser parameters are varied. The integration time can be set to be up to 20 seconds, such as 2, 10, or 15 seconds. The delay between scans can be set to be up to 40 seconds such as 5, 10, 15, 25, 30, or 35 seconds. The number of scans per sample can be set up to 20 scans per sample, such as 1, 3, 5, 10, or 15 scans.

Figure 17:
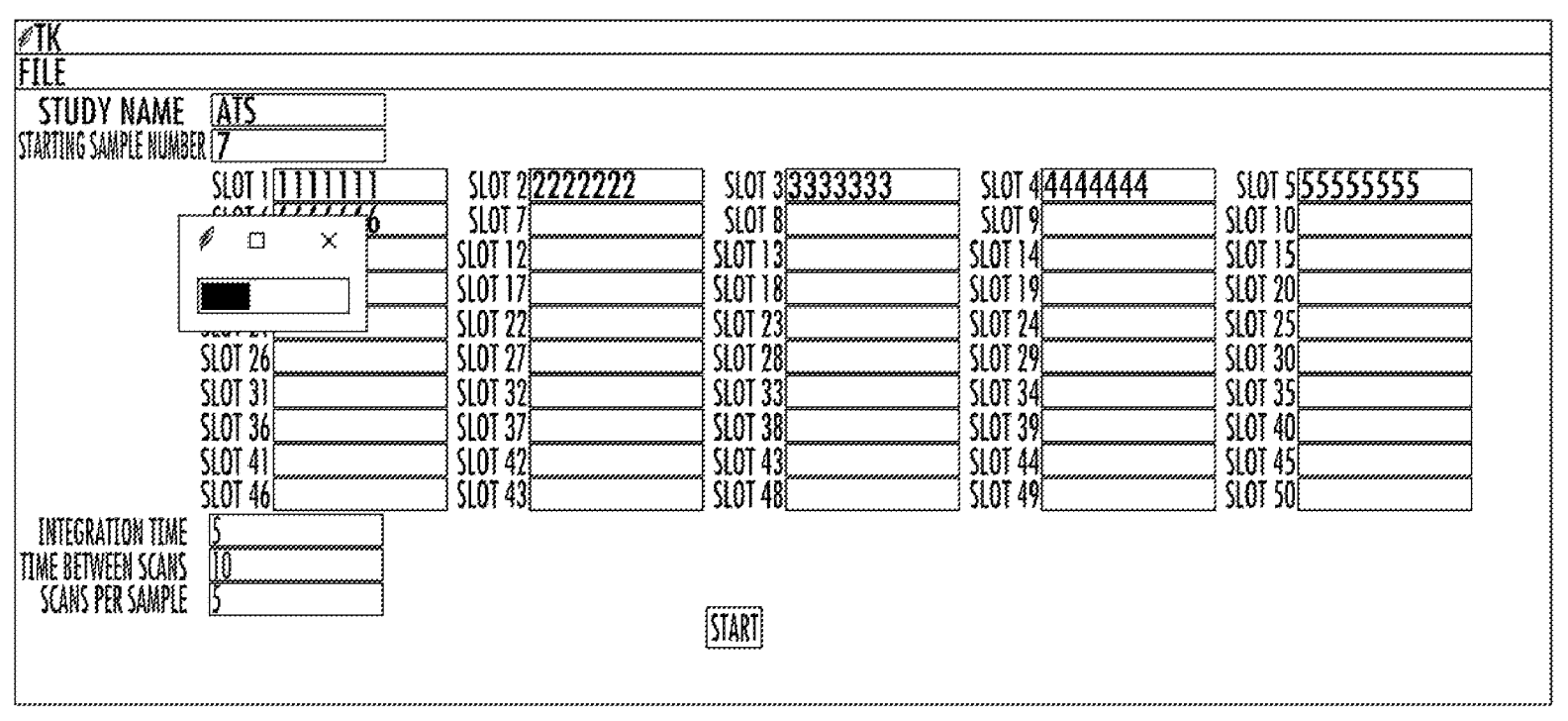
Figure 18:
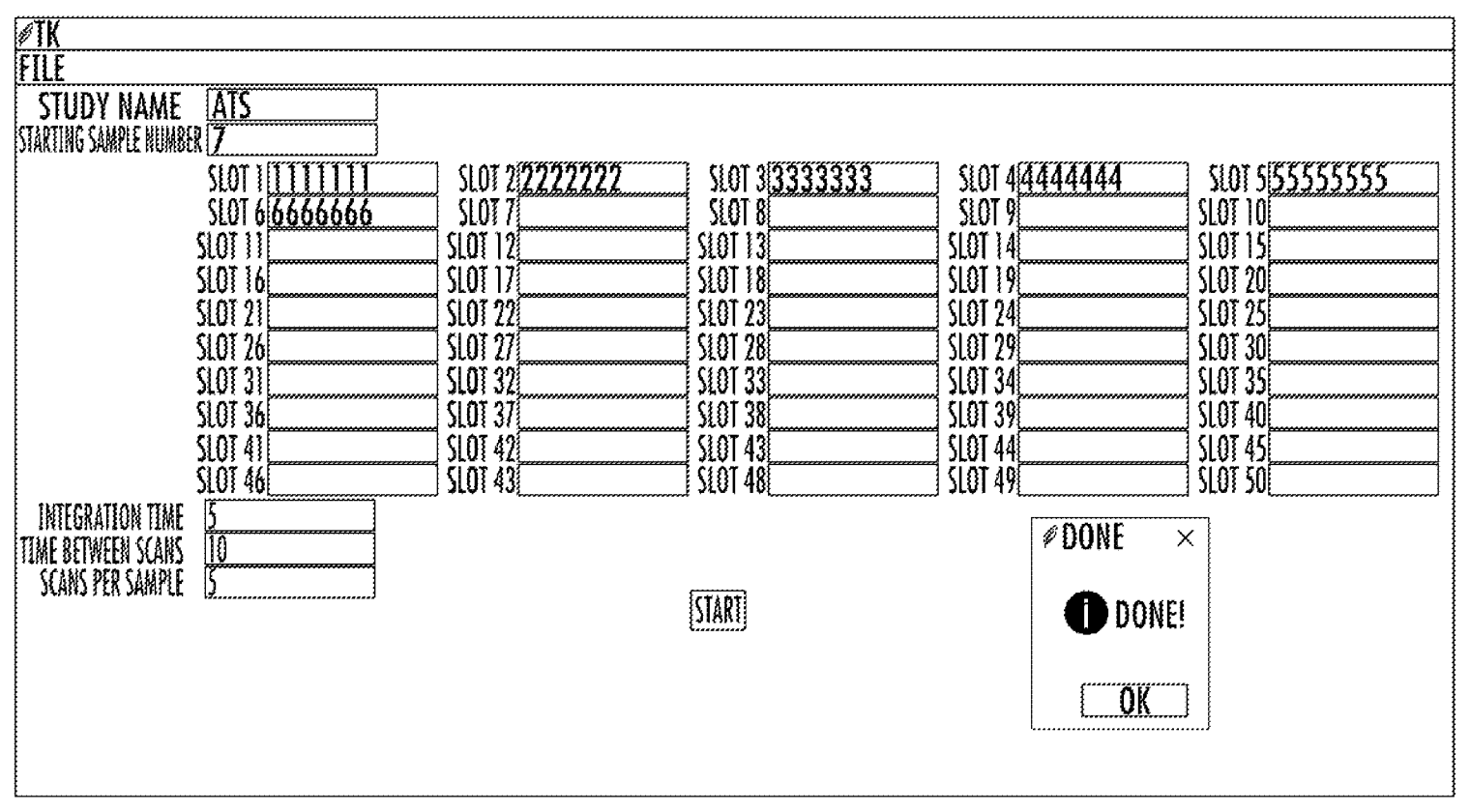

After clicking "Start", the GUI displayed a "Batch started" notification before generating a pop-up window with a progress bar that filled as the device scanned each sample that was input into the program (FIG. 17). When the run was complete and all samples were scanned, the GUI flashed another window, alerting the user that the batch was done. Then, the user could choose to download all data files using the "File" menu in the top left corner of the GUI (FIG. 18).

Figure 19:
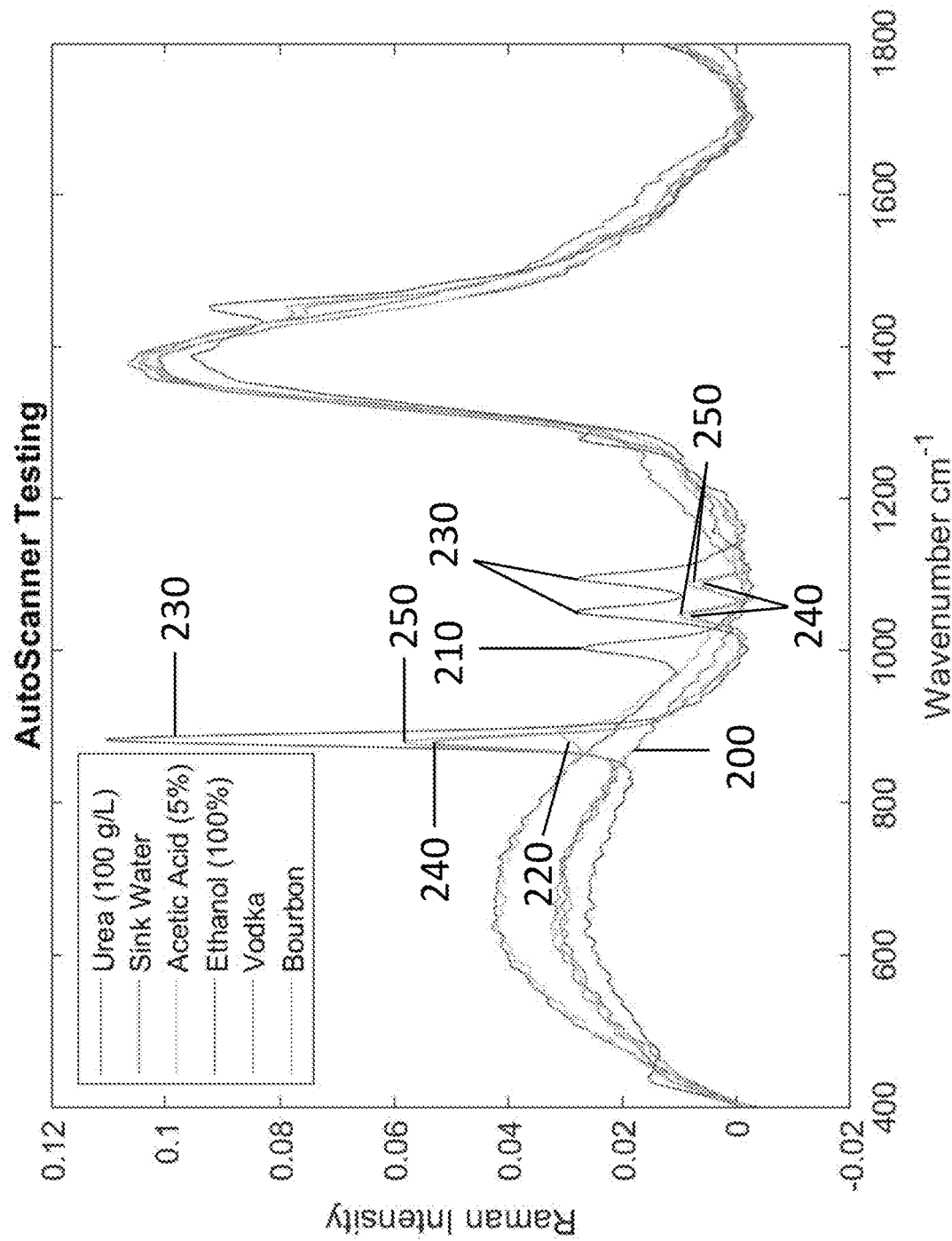
FIG. 19 is a graph showing the Raman plots for 6 fluid samples scanned automatically using the system according to an embodiment of the invention.

Though the automation of each individual device component and the complete control and communication of the GUI with the system appeared successful on the physical device, the generated data files were analyzed to verify the quality of the signal that was produced. FIG. 19 shows a RAMETRIX™ analysis of the six samples scanned. Each fluid has a unique spectra, but some similarities arise between the fluids with similar compositions. The sink water 200 provides the baseline with which to compare the urea in water 210 and diluted acetic acid 220. These spectra all follow a related trend, with unique peaks for urea and acetic acid appearing at 1000 cm$^{-1}$ and 900 cm$^{-1}$, respectively.

Likewise, the 100% ethanol sample 230 provides the baseline for the vodka 240 and bourbon 250 samples, with both liquids following the trend closely, though to a lesser amount because of their lesser alcohol quantity.

Figure 20:
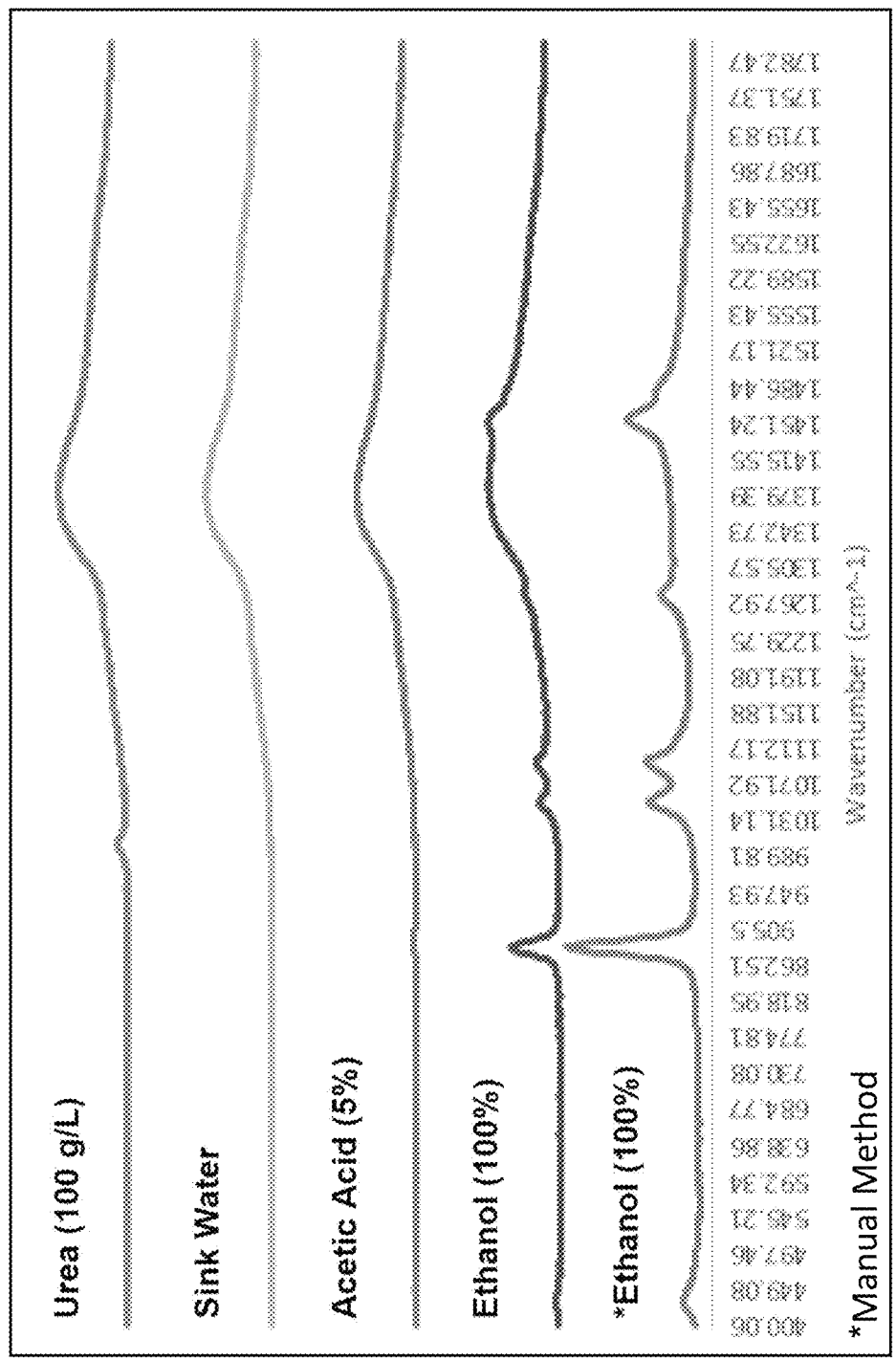
FIG. 20 is a graph showing a comparison of the Raman plots for 4 samples scanned automatically using the system and a single sample collected using a manual method.

To provide a simpler visual comparison of the water-based spectra, FIG. 20 was developed. This graph also indicates a comparison between the AutoScanner analysis results and the lab-scale, manual analysis results for the 100% ethanol sample. The AutoScanner data very nearly matches the data produced by the manual method (although the signal is less intense) and helps verify the functionality of the device.

EXAMPLE 2

Figure 21:
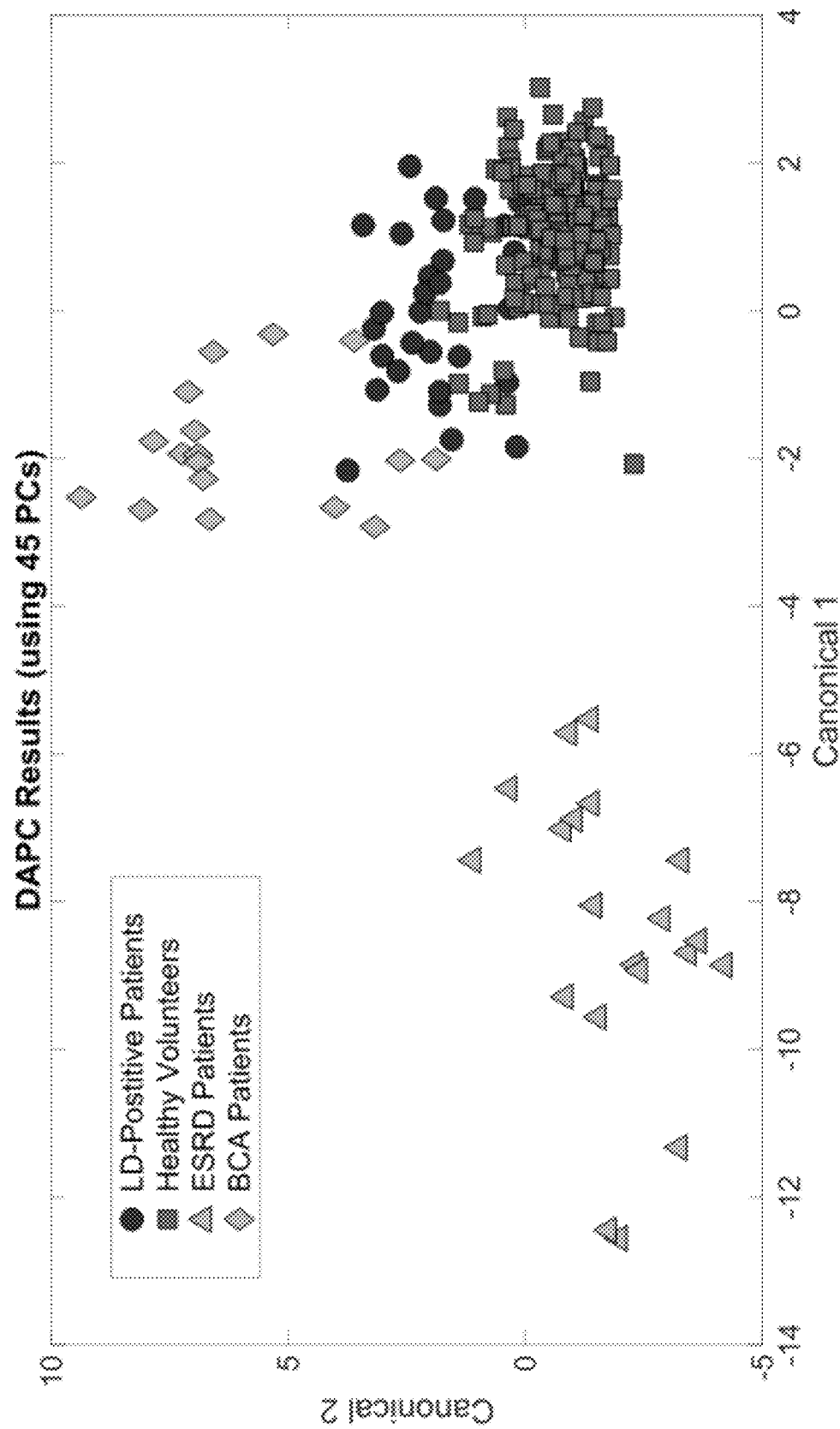
FIG. 21 is a graph showing a Rametrix™ LITE DAPC model built with 45 PCs (99.9% of the dataset variance) with urine spectra from LD-positive patients, CKD patients, BCA patients, and healthy human volunteers.

The AutoScanner can be used to screen patients for various diseases, including CKD. Raman spectra can be obtained for patient urine samples using the system according to embodiments of the invention. The data on the laptop/computer can be accessed and analyzed with the RAMETRIX™ software to determine significance. Exemplary methods for analyzing Raman spectra are described in U.S. patent application Ser. No. 17/146,301, entitled "METHODS OF DISEASE DETECTION AND CHARACTERIZATION USING COMPUTATIONAL ANALYSIS OF URINE RAMAN SPECTRA," filed Jan. 11, 2021 and which is hereby incorporated by reference herein in its entirety. The model can be constructed from various Raman spectra obtained from urine samples belonging to individuals that have or do not have the disease/condition of interest. With respect to water quality, for example, the model can be constructed from various Raman spectra obtained from water samples of various degrees of water quality. The Raman spectra can be baseline corrected and normalized. Next, analysis of the spectra is performed using principal component analysis (PCA). The patient data is compared to the model using discriminant analysis of principal components (DAPC) resulting in a classification of the sample as corresponding to a sample that has or does not have the specified disease/condition/quality. Example DAPC data is shown in FIG. 21. Data points belonging to healthy volunteers are clustered together away from the clusters of data points belonging to patients diagnosed with the various diseases. In this case, the model contains 45 principal components.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods, in whole or part, disclosed herein can be used with any of the systems, in whole or part, disclosed herein or with any other systems. Likewise, any of the disclosed systems, in whole or part, can be used with any of the methods, in whole or part, disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A system comprising:
   a Raman spectrometer;
   one or more sample carousel;
   a computer with a processor and memory;
   a component box for housing one or more components chosen from the Raman spectrometer, a laser, the computer, the processor, the memory, motor control(s) or power supply;
   wherein the component box is disposed under and as a support for one or more of the sample carousels; and
   one or more set of computer-executable instructions capable of:
      controlling the Raman spectrometer to obtain Raman spectral data on samples;
      controlling one or more of the sample carousels; and
      performing one or more chemometric analyses on the Raman spectral data.

2. The system of claim 1, wherein one or more of the chemometric analyses comprises identifying whether a urine sample is classified as being (a) from a subject who has a specified condition or (b) from a subject who does not have the specified condition, and is performed by determining that the Raman spectral data of the urine sample fits closer mathematically to one or the other statistically significant groups (a) or (b).

3. The system of claim 1, wherein the specified condition is any one or more of Bladder cancer (all types, grades, and stages); Acute cystitis (all types, grades, stages, and etiologies, including infectious and non-infectious etiologies); Chronic cystitis (all types, grades, stages, and etiologies, including infectious and non-infectious etiologies); Schistosomiasis; Kidney cancer (all types, grades and stages); Prostate cancer (all types, grades, and stages); Prostatitis (acute and chronic); Cervical cancer (all types, grades, and stages); Uterine cancer (all types, grades, and stages); Ovarian cancer (all types, grades, and stages); Cancer of the adrenal gland (all types, grades, and stages); Cushing's disease and Cushing's syndrome; Multiple myeloma with Bence-Jones proteinuria (all stages and grades); Acute kidney injury (all types and etiologies); Acute kidney failure (all types and etiologies); Chronic kidney failure (all types, stages, and etiologies); Acute glomerulonephritis (all types and etiologies); Chronic glomerulonephritis (all types and etiologies); Focal and diffuse segmental glomerulosclerosis (all stages, grades, and etiologies, including hypertension); Membranous nephropathy (all stages, grades, and etiologies); Membranoproliferative glomerulonephritis (all stages, grades, and etiologies, including systemic lupus erythematosus); Hemolytic uremic syndrome; IgA nephropathy (all stages, grades, and etiologies); Minimal change nephropathy (all stages, grades, and etiologies); Congenital nephropathy (all stages, grades, and etiologies); Diabetic nephropathy; Protein-losing nephropathy and nephrotic syndrome (all stages, grades, and etiologies); Acute pyelonephritis (all stages, grades, and etiologies); Chronic pyelonephritis (all stages, grade, and etiologies); Lyme disease (all stages and clinical presentations); Atypical borreliosis; Myalgic Encephalomyelitis/Chronic Fatigue Syndrome (ME/CFS) (all types, stages, and etiologies); Systemic mold allergy/toxicity; Hemobartonellosis; SARS-CoV-1 (Severe Acute Respiratory Syndrome Coronavirus Disease); SARS-CoV-2 (COVID-19 Disease); and MERS-CoV-2 (Middle Eastern Respiratory Syndrome Disease).

4. The system of claim 1, wherein one or more of the chemometric analyses comprises identifying a condition of a subject by:
   comparing the Raman spectral data on a urine sample of the subject to a selected model;
   wherein the selected model is constructed from various Raman spectra of urine from individuals having and not having a specified condition;
   wherein the comparing of the Raman spectra of the urine sample to the selected model comprises identifying whether the urine sample is classified according to the selected model as being urine either from a subject who has or does not have the specified condition.

5. The system of claim 4, wherein the selected model is constructed from:
   one or more multivariate analysis techniques applied to various Raman spectra of urine from individuals having and not having the specified condition;
   wherein one or more of the multivariate analysis techniques involves identifying statistically significant spectral differences between the urine from the individuals having the specified condition and those not having the specified condition.

6. The system of claim 1, wherein the memory has one or more reference set of Raman spectra stored thereon.

7. The system of claim 1, wherein one or more of the sample carousels is configured to hold up to 50 samples.

8. The system of claim 1, wherein the sample carousel is configured to accept vials, test tubes, specimen cups, and/or well plates.

9. The system of claim 1, wherein the computer-executable instructions are capable of controlling operation of and sequencing of the sample carousel, the Raman spectrometer and a laser in a manner such that (a) the sample carousel is capable of being rotated to present the sample in a first position, (b) then the laser is capable of interrogating the sample at the first position, and (c) then the Raman spectrometer is capable of generating Raman spectral data of the sample.

10. The system of claim 1, wherein the system is configured to test up to 400 samples per day.

11. The system of claim 9, wherein the computer-executable instructions are capable of controlling the Raman spectrometer to:
   administer a set number of scans per sample;
   apply a selected integration time; and/or
   administer the scans with a selected time delay between the scans.

12. The system of claim 1, wherein the system is configured to analyze liquid, solid, urine or water samples.

13. The system of claim 1, wherein the system is configured to obtain qualitative measurements.

14. The system of claim 1, wherein the system is configured to obtain quantitative measurements.

15. The system of claim 1, wherein the system is configured to analyze one or more sample using more than one excitation wavelength.

16. The system of claim 1, wherein the chemometric analyses on the Raman spectral data involves analyzing wavenumber clusters selected based on types of molecules expected relating to various pathologic features of a specified condition.

17. The system of claim 1, wherein:
   the Raman spectrometer uses a 785 nm laser for collecting the Raman spectral data; and
   the chemometric analyses on the Raman spectral data involves analyzing wavenumbers in one or more of the following ranges:
   urea band in the range of about 1,000 to 1,005 $cm^{-1}$, 1,002 $cm^{-1}$ and/or 1,003 $cm^{-1}$ bands,
   uric acid at 981 $cm^{-1}$,
   creatinine at 680 $cm^{-1}$,
   collagen at 870 $cm^{-1}$,
   glucose at 1,071 $cm^{-1}$ 1,117 $cm^{-1}$,
   phosphatidylinositol (576 $cm^{-1}$),
   nucleic acids (721, 827, 1340 $cm^{-1}$),
   protein (or collagen) (817, 981, 1065, 1127, 1340 $cm^{-1}$),
   aromatic amino acids (827, 1004 $cm^{-1}$),
   cholesterol and fatty acids (702, 1297 $cm^{-1}$),
   monosaccharides (846 $cm^{-1}$),
   glycogen (1048 $cm^{-1}$),
   carotenoids (1417, 1518 $cm^{-1}$),
   1,050-1,250 $cm^{-1}$ (lipids, carbohydrates, phosphate stretching, and C-N stretching of amides and proteins,
   1,590-1,750 $cm^{-1}$ (protein assignments, namely to aromatic amino acids),
   669, 750, 752, 999, 1,122, 1,210, 1,444, 1,543, 1,579, 1,617 $cm^{-1}$ (heme and red blood cells),
   around 900 $cm^{-1}$ and from 1,200-1,400 $cm^{-1}$ (associated with tryptophan and protein, including collagen),
   620 $cm^{-1}$ (related to aromatics),
   880 $cm^{-1}$, 1,360 $cm^{-1}$, 1,364 $cm^{-1}$ (tryptophan),
   642 $cm^{-1}$, 665 $cm^{-1}$ (related to tyrosine), and/or
   1,211 $cm^{-1}$ (tyrosine and phenylalanine).

18. A method of identifying a condition of a subject, comprising:
   obtaining Raman spectra from a urine sample from a subject using the system of claim 1;
   comparing the Raman spectra of the urine sample to a selected model;
   wherein the selected model is constructed from various Raman spectra of urine from individuals having and not having a specified condition; and
   wherein the comparing of the Raman spectra of the urine sample to the selected model comprises identifying whether the urine sample is classified according to the selected model as being urine either from a subject who has or does not have the specified condition;
   wherein the selected model is constructed from:
   one or more multivariate analysis techniques applied to various Raman spectra of urine from individuals having and not having a specified condition;
   wherein one or more of the multivariate analysis techniques involves identifying statistically significant spectral differences between the urine from the individuals having the specified condition and those not having the specified condition.

* * * * *